(12) United States Patent
Srivastava et al.

(10) Patent No.: US 8,309,707 B2
(45) Date of Patent: *Nov. 13, 2012

(54) RNA SYNTHESIS-PHOSPHORAMIDITES FOR SYNTHETIC RNA IN THE REVERSE DIRECTION, AND APPLICATION IN CONVENIENT INTRODUCTION OF LIGANDS, CHROMOPHORES AND MODIFICATIONS OF SYNTHETIC RNA AT THE 3'-END

(75) Inventors: Suresh C. Srivastava, Burlington, MA (US); Divya Pandey, Lucknow (IN); Satya P Bajpai, Lucknow (IN); Naveen P Srivastava, Burlington, MA (US)

(73) Assignee: ChemGenes Corporation, Wilmigton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/584,625

(22) Filed: Sep. 8, 2009

(65) Prior Publication Data

US 2010/0324278 A1    Dec. 23, 2010

Related U.S. Application Data

(60) Provisional application No. 61/191,065, filed on Sep. 6, 2008.

(51) Int. Cl.
*C07H 21/00* (2006.01)
*C07H 19/20* (2006.01)
*C07H 19/10* (2006.01)
*C07H 19/048* (2006.01)

(52) U.S. Cl. .............. 536/25.34; 536/26.7; 536/26.8

(58) Field of Classification Search .............. None
See application file for complete search history.

(56) References Cited

OTHER PUBLICATIONS (R) Van Boom et al., "Chemical Synthesis of Small Oligoribonucleotides in Solution," Ch. 7 in Oligonucleotide Synthesis—A Practical Approach, M. J. Gait (ed.), IRL Press, Washington, DC, 1984, only pp. 153-183 supplied.*

(S) Beckett et al., "Enzymatic Synthesis of Oligoribonucleotides," Ch. 8 in Oligonucleotide Synthesis—A Practical Approach, M. J. Gait (ed.), IRL Press, Washington, DC, 1984, only pp. 184-197 supplied.*

Guzaev et al., "A Conformationally Preorganized Universal Solid Support for Efficient Oligonucleotide Synthesis," J. Amer. Chem. Soc., 125(9), 2380-2381 (2003): CAPlus Abstract No. 2003:98281, CA Doc. No. 138: 287895: see CAPLUS search of record for Abstract and structure.*

(U) Anon., Sigma Catalog—Biochemicals and Reagents, St. Louis, MO, 2002-2003: only p. 1424 supplied, see items R 4142 and R 6895.*

* cited by examiner

*Primary Examiner* — Lawrence E Crane

(74) *Attorney, Agent, or Firm* — Law Offices of Indu M. Anand

(57) ABSTRACT

Novel technology for RNA synthesis in the reverse direction, involving a new class of products, 3'-DMT-5'-CE ribonucleoside phosphoramidites and 3'-DMT-5'-succinyl ribonucleoside solid supports, with per step coupling efficiency surpassing 99% in the RNA synthesis. This leads to high purity RNA. Examples of a large number of 20-21 mers and a few examples of long chain oligonucleotides are demonstrated. The data indicates dramatic improvement in coupling efficiency per step during oligonucleotide synthesis using the reverse RNA monomers (5'→' direction) as compared to 3'-CE ribonucleoside phosphoramidites used in the conventional method of RNA synthesis (3'→5' direction). The new process requires shorter coupling cycle time, approx. 4 minutes as compared to approx. 10 minutes using conventional RNA synthesis method (3'→5' direction). Furthermore, almost complete absence of M+1 impurities in the reverse RNA synthesis methodology were observed, even when the last phosphoramidite was a macromolecule. The process resulted in very high purity 3'-modified oligonucleotides after HPLC purification. As a result of high purity of synthesized RNA and clean introduction of various 3'-end modified RNA requiring long chain ligands, chromophores, fluorophores and quenchers, this method of RNA synthesis is expected to be a very useful method of choice for therapeutic grade RNA. The novel phosphoramidites of this invention, Rev-A-n-bz, Rev-C-n-bz, Rev-C-n-ac, Rev-G-n-ac and Rev-rU show HPLC purity greater than 98% and $^{31}P$ NMR purity greater than 99.5%.

3 Claims, 21 Drawing Sheets

Average Stepwise Yield: 99.6% Using Sequence Leveling
21-mer RNA Synthesized with 3'-DMT 2'tBDSilyl-5'CED Phosphoramidites

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Completely Synthesized

<400> SEQUENCE: 1

```
caggugcaga gccuugccct t                                                21

<210> SEQ ID NO 2
<211> LENGTH: 21
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (21)..(21)
<223> OTHER INFORMATION: Cholesterol TEG is attached to terminal
      nucleotide

<400> SEQUENCE: 2
caggugcaga gccuugccct t                                                21

<210> SEQ ID NO 3
<211> LENGTH: 21
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (21)..(21)
<223> OTHER INFORMATION: PEG-2000 is attached to terminal nucleotide

<400> SEQUENCE: 3
caggugcaga gccuugccct t                                                21

<210> SEQ ID NO 4
<211> LENGTH: 21
<212> TYPE: DNA
<213> ORGANISM: Artificial Sequence
<220> FEATURE:
<223> OTHER INFORMATION: Completely Synthesized
<220> FEATURE:
<221> NAME/KEY: misc_feature
<222> LOCATION: (21)..(21)
<223> OTHER INFORMATION: Hexaethyloxyglycol (HEG) is attached to
      terminal nucleotide

<400> SEQUENCE: 4
caggugcaga gccuugccct t                                                21
```

RNA SYNTHESIS-PHOSPHORAMIDITES FOR SYNTHETIC RNA IN THE REVERSE DIRECTION, AND APPLICATION IN CONVENIENT INTRODUCTION OF LIGANDS, CHROMOPHORES AND MODIFICATIONS OF SYNTHETIC RNA AT THE 3'-END

CROSS-REFERENCE TO OTHER APPLICATIONS

This application claims priority from the Provisional Patent Application, Ser. No. 61/191,065, filed by the same inventors on Sep. 6, 2008. The entire contents of the prior provisional application are incorporated herein by reference.

No new matter beyond the disclosure of the provisional applications has been introduced herein. However, new drawings, FIGS. 6a, 6b and 9a, and an additional example based on previously described experimentation have been added, and Brief Description of the Drawings updated.

FIELD OF THE INVENTION

This invention relates to the synthesis of novel RNA monomer phosphoramidites, and corresponding solid supports that are suitable for a novel method of RNA oligonucleotide synthesis in reverse 5'→3' direction. This approach leads to very clean oligonucleotide synthesis allowing for introduction of various modifications at the 3'-end cleanly and efficiently in order to produce high purity and therapeutic grade RNA oligonucleotides.

BACKGROUND OF THE INVENTION

Defined sequence RNA synthesis in the 3'→5' direction is now well established and currently in use for synthesis and development of a vast variety of therapeutic grade RNA aptamers, tRNA's, siRNA and biologically active RNA molecules. This approach utilizes a ribonucleoside with suitable N-protecting group: generally 5'-Protecting group, the most popular being dimethoxytriphenyl, i.e. the DMT group; 2'-protecting group, out of which most popular is t-Butyldimethylsilyl ether; and, a 3'-phosphoramidite, the most popular of which is cyanoethyl diisopropyl (component 1). This component is then coupled with a nucleoside with a suitable N-protecting group, 2' or 3' succinate of a ribonucleoside attached to a solid support (component 2). The coupling of component 1 and 5'-OH-n-protected-2',3'-protected-nucleoside (component 3) are also achieved in solution phase in presence of an activator to lead to dimers and oligoribonucleotides, followed by oxidation (3'→5' direction synthesis), also lead to protected dinucleoside having a 3'-5'-internucleotide linkage, Ogilvie, K. K., Can. J. Chem., 58, 2686, 1980 (scheme 1).

However, the synthesis of RNA in the reverse direction (5'-3' direction) has not been achieved so far to the best of our knowledge.

The 2'-silyl ethers of component 1 have been developed extensively and they are known to have remarkable stability. Solvolysis of silyl ethers have been extensively studied and it is known that bulky alkyl silyl ethers have a high degree of stability; Bazani, B and Chvalowski, V Chemistry of Organosilicon compounds, Vol. 1, Academic Press, New York, 1965. Extensive research work was subsequently done by Ogilvie and coworkers as 2'-hydroxy protecting group for oligo ribonucleotide synthesis (Ogilvie, K. K., Sadana, K. L, Thompson, E. A., Quilliam, M. A., and Westmore, J. B Tetrahedron Letters, 15, 2861-2864, 1974; Ogilvie, K. K., Beaucage, S. L, Entwistle, D. W., Thompson, E. A., Quilliam, M. A., and Westmore, J. B. J. Carbohydrate Nucleosides Nucleotides, 3, 197-227, 1976; Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256, 1983).

These studies subsequently led to continued developments of methods which were amenable to both solution and solid phase oligonucleotide synthesis, and the first chemical synthesis of RNA molecules of the size and character of tRNA (Usman, N., Ogilvie, K. K., Jiang, M.-Y.,and Cedergren, R. J. J. Am. Chem. Soc. 109, 7845-7854, 1987; Ogilvie, K. K., Usman, N., Nicoghosian, K, and Cedergren, R. J. Proc. Natl. Acad Sci. USA, 85, 5764-5768, 1988; Bratty, J., Wu, T., Nicoghosian, K., Ogilvie, K. K., Perrault, J.-P., Keith, G. and Cedergren, R., FEBS Lett. 269, 60-64, 1990). The literature has been amply reviewed in subsequent excellent publication: Gait, M. J., Pritchard, C. and Slim, G., Oligonucleotides and Their Analogs: A Practical Approach (Gait, M. J., ed.), Oxford University Press Oxford, England, pp 25-48, 1991. Other protecting groups which have been lately employed for RNA synthesis are: bis(2-acetoxyethyl-oxy)methyl (ACE), Scaringe, S. A., Wincott, F. E., Caruthers, M. H., J. Am. Chem. Soc., 120: 11820-11821, 1998; triisopropylsilyloxy methyl (TOM), Pitsch, S., Weiss, P. A., Jenny, L., Stutz, A., Wu, X., Hely. Chim. Acta. 84, 3773-3795, 2001 and t-butyldithiomethyl (DTM) (structure 1), Semenyuk, A., Foldesi, A., Johansson, T., Estmer-Nilsson, C., Blomgren, P., Brannvall, M., Kirsebom, L. A., Kwiatkowski, M., J. Am. Chem. Soc., 128: 12356-12357, 2006 have been introduced. However, none of these processes is amenable to carry out the synthesis of RNA in reverse direction (5'→3'direction); hence they lack the capability of the convenient and efficient introduction of many ligands and chromophores at the 3'-end of RNA molecules, achievable through reverse direction synthesis.

Chemically modified RNA have been synthesized having modified arabino sugars, 2'-deoxy-2'-fluoro-beta-D_arabinonucleic acid (FANA; structure 2)) and 2'-deoxy-4'-thio-2'-fluoro-beta-D_arabinonucleic acid (4'-Thio-FANA; structure 3) into sequences for siRNA activities, Dowler, T., Bergeron, D., Tedeschi, Anna-Lisa, Paquet, L., Ferrari, N., Damha, M. J. Nucl. Acids Res., 34, 1669-1675, 2006. Amongst the several new 2'-protecting groups the chemistry for which have been developed, the 2'-protecting 2-cyanoethoxymethyl (CEM) (structure 4) has been shown for producing very long RNA, however, which also carries out RNA synthesis in the conventional, i.e., the 3'→5'direction. Furthermore, the quality of RNA produced by these processes remains in question.

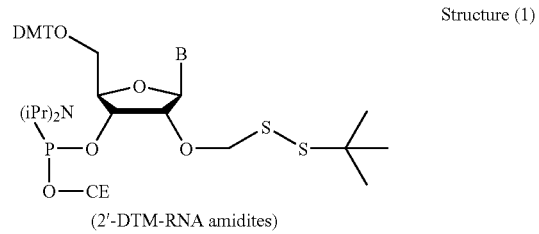

(2'-DTM-RNA amidites)

Structure (1)

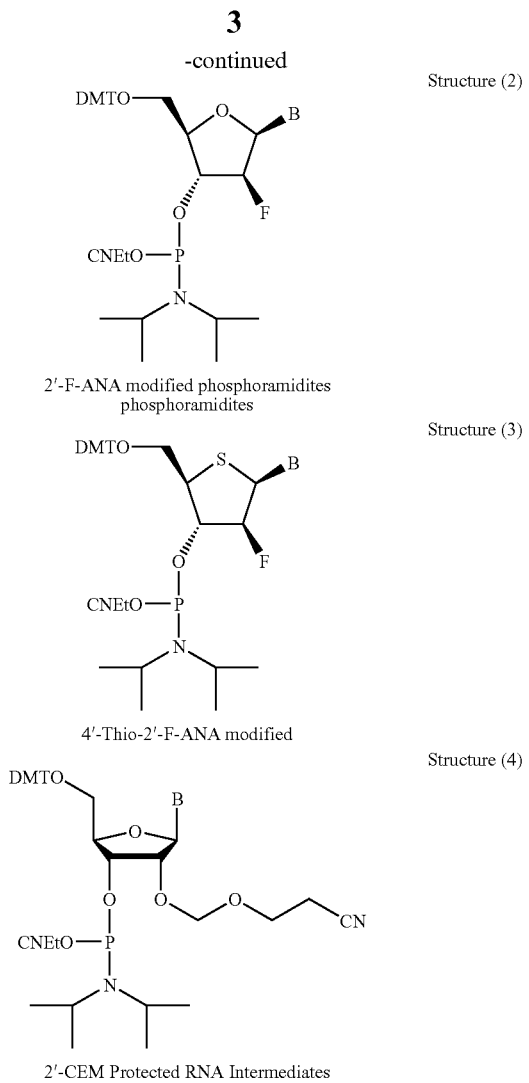

Structure (2)

2'-F-ANA modified phosphoramidites
phosphoramidites

Structure (3)

4'-Thio-2'-F-ANA modified

Structure (4)

2'-CEM Protected RNA Intermediates

The chemical synthesis of RNA is desirable because it avoids the inefficiencies and limitation of scale of synthesis such as by in vitro transcription by T7 RNA polymerase, Helm, M., Brule, H., Giege, R., Florence, C., RNA, 5:618-621, 1999. Chemical synthesis of RNA is desirable for studies of RNA structure and function, and many useful modifications can be achieved selectively, such as site specific introduction of functional groups; viz., disulphide cross linking as a probe of RNA tertiary structures, Maglott, E. J., Glick, G. D., Nucl. Acids Res., 26: 1301-1308, 1999.

Synthesis of long RNA is very important for biologically active molecules such as tRNA, and such synthesis has been achieved; Persson, T., Kutzke, U., Busch, S., Held, R., Harmann, R. K., Bioorgan. Med. Chem., 9:51-56, 2001; Ogivie, K. K., Usman, N., Nicoghosian, K., Cedrgren, R. J., Proc. Natl. Acad. Sci., USA, 85:5764-5768, 1988; Bratty, J., Wu, T., Nicoghosian, K., Ogilvie, K. K., Perreault, J.-P., Keith, G., Cedergren, R. J., F.E.B.S. Lett., 269:60-64, 1990; Gasparutto, D., Livache, T., Bazin, H., Duplaa, A. M., Guy, A., Khorlin, A., Molko, D., Roget, A., Teoule, R., Nucl. Acids. Res., 20:5159-5166, 1992; Goodwin, J. T., Stanick, W. A., Glick, G. D., J. Org. Chem., 59:7941-7943, 1994. None of the techniques mentioned in this paragraph, however contemplate the synthesis of RNA in reverse direction (5'→3'direction), and hence the practical and convenient introduction of a number of groups required for selective introduction at 3'-end remains elusive.

The present inventors have observed higher coupling efficiency per step during automated oligo synthesis with our reverse RNA amidites, resulting in a greater ability to achieve higher purity and produce very long oligos. They also demonstrate that the process of this invention leads to oligonucleotides free of M+1 species, which species lead to closer impurities as shoulder of desired peak during HPLC analysis or purification or Gel purification.

The t-butyldimethyl silyl protecting group on 2'-hydroxyl of ribonucleosides has been the group of choice for making 3'-phosphoramidites and for utilizing them for oligonucleotide synthesis which have been shown to migrate to 3'-hydroxyl position rather easily. This has been documented amply and in detail (Ogilvie, K. K., and Entwistle, D. W. Carbohydrate Res., 89, 203-210, 1981; Wu, T., and Ogilvie, K. K. J. Org. Chem., 55, 4717-4734, 1990). Such migration complicates the synthesis of the desired phosphoramidites and requires an efficient method of purification that clearly resolves corresponding isomers and prevents any contamination of the final monomer.

The present invention is directed towards the synthesis of high purity RNA's, specifically to introduce selected groups at 3'-end of oligonucleotides of synthetic RNA's. Such RNA's have vast application in therapeutics, diagnostics, drug design and selective inhibition of an RNA sequence within cellular environment, blocking a function of different types of RNA present inside cell.

Silencing gene expression at mRNA level with nucleic acid based molecules is a fascinating approach. Among these RNA interference (RNAi) has become a proven approach which offers great potential for selective gene inhibition and shows great promise for application in the control and management of various biochemical and pharmacological processes. Early studies by Fire et al., Fire, A., Xu, S., Montgomery, M. K., Kostas, S. A., Driver, S. E., and Mello, C. C, Nature, 391, 806-811, 1998, showed that RNA interference in Caenorhabditis elegans is mediated by 21 and 22 nucleotide RNA sequences. This was further confirmed as a general phenomenon of specific inhibition of gene expression by small double stranded RNA's being mediated by 21 and 22 nucleotide RNA's, Genes Dev., 15, 188-200, 2001. Simultaneous studies by Capie, N. J., Parrish, S., Imani, F., Fire, A., and Morgan, R. A., confirmed such phenomenon of specific gene expression by small double stranded (dS) RNAs in invertebrates and vertebrates alike. Subsequently a vast amount of research led to the confirmation of above studies and established RNAi as a powerful tool for selective, and very specific gene inhibition and regulation; Nishikura, K., Cell, 107, 415-418, 2001; Nykanen, A., Haley, B., Zamore, P. D., Cell, 107, 309-321, 2001; Tuschl, T., Nat. Biotechnol., 20, 446-448, 2002; Mittal, V., Nature Rev., 5, 355-365, 2004; Proc. Natl. Acad. Sci. USA, 99, 6047-6052, 2002; Donze, O. & Picard, D., Nucl. Acids. Res., 30, e46,2002; Sui, G., Soohoo, C., Affar el, B., Gay, F., Shi, Y., Forrester, W.c., and Shi, Y., Proc. Natl. Acad. Sci. USA, 99, 5515-5520, 2002; Paddison, P. J., Caudy, A. A., Bernstein, E., Hannon, G. J.; and Conklin, D. S., Genes Dev., 16, 948-959, 2002.

Besides the natural double stranded (ds) RNA sequences, chemically modified RNA have been shown to cause similar or enhanced RNA interference in mammalian cells using 2'-deoxy-2'-fluoro-beta-D_arabinonucleic acid (FANA) into sequences for siRNA activities, Dowler, T., Bergeron, D., Tedeschi, Anna-Lisa, Paquet, L., Ferrari, N., Damha, M. J., Nucl. Acids. Res., 34, 1669-1675, 2006.

Various other modifications to improve siRNA properties have been pursued, which include alteration in backbone chemistry, 2'-sugar modifications, and nucleobase modifications, some of which have been recently reviewed; Nawrot, B, and Sipa, K., Curr. Top. Med. Chem., 6,913-925, 2006; Manoharan, M. Curr. Opin. Chem. Biol., 8, 570-579, 2004. The PS modifications of siRNA are well tolerated, although some reports indicate increased toxicity and somewhat reduced efficacy; Harborth, J., Elbasir, S. M., Vandenburgh, K., Manninga, H., Scaringe, S. A., Weber, K., Tuschl, T., Antisense Nucleic Acid Drug Dev., 13, 83-105, 2003. Among these is also the 2'-Omethyl modification, although it maintains A form (RNA like) helix, and has been shown to be either retaining or reducing siRNA activity depending on the number of such modifications within a sequence, Chiu, Y. L., Rana, T. M., RNA, 9, 1034-1048, 2003. It has also been shown that extensive 2'-O-Methyl modification of a sequence can be made in the sense strand without loss of siRNA activity, Kraynack, B. A., Baker, B. F., RNA, 12, 163-176, 2006.

Bicyclic locked nucleic acids (LNA's) that confer high binding affinity have also been introduced in siRNA sequences, especially when the central region of siRNA sequence is avoided, Braash, D. A., Jensen, S., Liu, Y., Kaur, K., Arar, K., White, M. A., and Corey, D. R., Biochemistry, 42, 7967-7995, 2003. Similarly altritol sugar modified oligonucleotides (ANA) have recently been reported. Altrilol sugar offers a rigid conformation and is shown to form very stable duplexes with RNA in a sequence specific manner, and further shown to stay in A (RNA type) conformation. It was shown that ANA modified siRNAs targeting MDR1 gene exhibited improved efficacy as compared to unmodified controls, specifically effective when this modification was near the 3'-end of sense or antisense strand; Fisher, M., Abramov, M., Aerschot, A. V., Xu, D., Juliano, R. L., Herdewijn, P., Nucl. Acids Res., 35, 1064-1074, 2007.

Among the various requirements for effective RNA interference (RNAi) to take place, a number of observations and facts have been established. Thus the RNA has to be double stranded (ds)) in the region of identity to the target. For the chemical requirement, besides the capability of 5'-end to be converted to triphosphates, modifications of A, C, G were found to be fully compatible with interference activity. Backbone modification of RNA, such as 2'-fluoro, 2'-amino uracil, 2'-deoxy thymidine, and 2'-deoxycytidine appear to stabilize the modified RNA in the resulting double strand. Amongst the nucleoside base modification 5-bromouracil, 4-thiouracil, 5-iodouracil, 5-(3-aminoallyl)-uracil, inosine are readily incorporated in the RNA intereference complex (RNAi & RISC complex). Similarly inosine may be substituted for guanosine.

It has been shown that cholesterol-conjugated siRNA can achieve delivery into cells and silence gene expression. Further, it has been shown that lipid conjugated siRNA, bile acids, and long chain fatty acids can mediate siRNA uptake into cells and silence gene expression in vivo. Efficient and selective uptake of siRNA conjugates in tissues is dependent on the maximum association with lipoprotein particles, lipoprotein/receptor interactions and transmembrane protein mediated uptake. It has been shown that high density lipoproteins direct the delivery of of siRNA into liver, gut, kidney and steroidal containing organs. It has been further shown that LDL directs siRNA primarily to the liver and that LDL receptor is involved in the delivery of siRNA. These results show great promise for siRNA uptake by an appropriate delivery system which can be exploited in development of therapeutics. (Article by Marcus Stoffel, OTS, 2007, p. 64.)

It has been proposed that siRNA can be designed with chemical modifications to protect against nuclease degradation, abrogate inflammation, reduce off target gene silencing, and thereby improve effectiveness for target genes. Delivery vehicles or conjugates of lipids and other lipophilic miolecules which allow enhanced cellular uptake are essential for therapeutic developments. Such siRNA's are presently being developed for human target validation, interfering with diseases pathways and developing new frontier for drug development. Alan Sachs, Merck, Oligonucleotide Therapeutics Conference (OTS), page 80, 2007.

The 3'-end of sense strand of siRNA can be modified and has been shown to tolerate modification, and that attachment of ligands is most suited at this end (FIGS. 1 & 2), as detailed in a number of key publications; siRNA function in RNAi: a chemical modification, Ya-Lin Chiu and Tariq Rana, RNA, 9, 1034-1048, 2003; M. Manoharan, Curr. Opin. Chem. Biol, 6, 570-579, 2004; Nawrot, B. and Sipa, K., Curr. Top. Med. Chem., 6, 913-925, 2006; Scaringe, S., Marshall, W. S., Khvorova, A., Naty. Biotechnol., 22, 326-30, 2004.

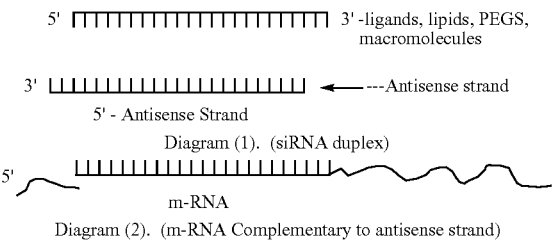

Diagram (1). (siRNA duplex)

Diagram (2). (m-RNA Complementary to antisense strand)

The introduction of lipophilic or hydrophobic groups and enhancing of siRNA delivery and optimization of targets has been addressed and achieved through bio-conjugation (Diagram 1). Generally the attachment is done, preferably at the 3'-end of senses strand, and occasionally on the 3'-end of the antisense strand. The design of nuclease resistant siRNA has been the subject of intense research and development recently in order to develop effective therapeutics. Thus base modifications such as, 2-thiouridine, pseudouridine, dihydrouridine have revealed the effect on conformations of RNA molecules and the associated biological activity; Sipa, K., Sochacka, E., Kazmierczak-Baranska, J., Maszewska, M., Janicka, M., Nowak, G., Nawrot, B., RNA, 13, 1301-1316, 2007. It was shown that 2'-modified RNA's especially 2'-Fluoro have great resistance towards nuclease and are biological active in-vivo, Layzer, J. M., McCaffrey, A. P., Tanner, A. K., Huang, Z., Kay, M. A., and Sullenger, B. A., RNA, 10, 766-771, 2004. 2'-O-Alkyl-modification, such as 2'-Omethyl's and 2'-O-MOE, Prakash, S., Allerson, C V. R., Dande, P., Vickers, T. A., Siofi, T. A., Jarres, R., Baker, B. F., Swayze, E. E., Griffey, R. H., and Bhat, B., J. Med. Chem., 48, 4247, 4253, 2005. The same authors used 4'-thio modified sugar nucleosides in combination of 2'-O alkyl modification for improving siRNA properties and RNAi enhancement, Dande, P., Prakas, T. P., Sioufi, N., Gaus, H., Jarres, R., Berdeja, A., Swayne, E. E., Griffey, R. H., Bhat, B. K, J. Med. Chem., 49, 1624-1634, 2006. The Replacement of internucleotide phosphate with phosphorothioate and boranophosphates of siRNAs show promise in-vivo, Li, Z. Y., Mao, H., Kallick, D. A., and Gorenstein, D. G., Biochem. Biophys. Res. Comm., 329, 1026-1030, 2005; Hall, A. H. S., Wan, J., Shaughnessy, E. E., Ramsay Shaw, B., Alexander, K. A., Nucl. Acids Res., 32, 5991-6000, 2004.

Bioconjugation of siRNA molecules, biologically RNA molecules, aptamers and synthetic DMNA molecules require, in addition to in vivo stability and appropriate modification of nucleosides, a key feature for cell membrane permeability: Insufficient cross-membrane cellular uptake limits the utility of siRNA's, other single stranded RNA's or even various DNA molecules. Thus cholesterol attached at 3'-end of siRNA has been shown to improve in-vivo cell trafficking and therapeutic silencing of gene, Soutschek, J., Akine, A., Bramlage, B., Charisse, K., Constein, R., Donoghue, M., Elbasir, S., Geickk, A., Hadwiger, P., Harborth, J., Nature, 432, 173-0178, 2004.

Among the various conjugations, besides cholesterol, which have been developed are:

(a) Natural and synthetic protein transduction domains (PTDs), also called cell permeating peptides (CPPs) or membrane permeant peptides (MPPs) which are short amino acid sequences that are able to interact with the plasma membrane. The uptake of MPP-siRNA conjugates takes place rapidly. Such peptides can be conjugated preferably to the 3'-of stand strand.

(b) Other polycationic molecules can be conjugated at the 3'-end of either sense or antisense strand of RNA.

(c) PEG (polyethylene glycols-oligonucleotide conjuagates) have been used in various complex possess significant gene silencing effect after uptake in target cells, Oishi, M., Nagasaki, Y., Itaka, K., Nishiyama, N., and Kataoka, K., J. Am. Chem. Soc., 127, 1624-1625, 2005.

(d) Aptamers have been used for site specific delivery of siRNA's. Since

Aptamers have high affinity for their targets, the conjugates with siRNA act as excellent delivery system, which result in efficient inhibition of the target gene expression, Chu, T. C., Twu, K. Y., Ellington, A. D. and Levy, M., Nucl. Acids Res., 34(10), e73, 2006. These molecues can once again be conjugated at the 3'-end of siRNA or other biologically active oligonucleotides.

(e) Various lipid conjugations at the 3'-end can be achieved through the present invention and can be utilized for efficient internalization of oligonucleotides. The lipophilic moiety can consist of a hydroxyl function to synthesize a phopsphoramidite. Similarly the lipophilic moiety can have carboxylic function at the terminus. The later can be coupled to a 3'-amino group having a spacer, synthesized by last addition of amino linkers such as C-6 amino linker amidite, of the reverse synthesized oligonucleotide, to the carboxylic moiety using DCC (dicyclohexyl cabodiimide) or similar coupling reagent.

This research has been reviewed elegantly by Paula, De. D., Bentley, M. V. L. B., Mahao, R. L., RNA, 13, 431-456, 2007.

Another class of RNA, closely related to siRNA are microRNA, commonly referred as miRNA. These are a large class of non coding RNA's which have a big role in gene regulation, Bartel, D. P. Cell, 116,281-297, 2004; He, L., Hannon, G. J. Nat. Rev. Genet, 5:522-531, 2004; Lagos-Quintana, M., Rauhut, R., Lendeckel, W., Tuschl, T., Science, 204:853-858,2001. In human genome there are at least 1000 miRNA scattered across the entire genome. A number of these micro RNA's down regulate large number of target mRNAs, Lim, L. P., Lau, N. C., Garrett-Engele, P., Grimson, A., Schelter, J. M., Castle, J., Bartel, D. P., Linsey, P. S., Johnson, J. M., Nature, 433:769-773, 2005. Different combination of miRNAs are possibly involved in the regulation of target gene in mammalian cell. It has also been shown that siRNA can function as miRNAs; Krek, A., Grun, D., Poy, M. N., Wolf, R., Rosenberg, L., Epstein, E. J., MacMenamin, P., da Piedade, I., Gunsalus, K. C., Stoffel, M., Nat. Genet., 37: 495-500, 2005; Doench, J. G., Petersen, C. P., Sharp, P. A., Genes Dev., 17:438-442, 2003. The miRNA have great potential in therapeutics and in gene regulation, Hammond, S. M., Trends Mol. Med. 12:99-101, 2006. A vast amount of effort is being currently devoted towards understanding miRNA pathways, their role in development and disease, focusing specially on cancer. The miRNA targets are being developed for therapeutic and diagnostics development. A great number of miRNA are being identified and their role is being determined through microarrays, PCR and informatics. Syntheses of RNA designed to target miRNA also require RNA synthesis and other modification as required for siRNA's, for the stability of RNA and the bioconjugation for better cellular uptakes. The reverse synthesis envisioned by the present invention can greatly accelerate the pace of this research and development.

Synthesis of vast variety of therapeutic grade RNA and siRNA requires a modification or labeling of 3'-end of an oligonucleotide. In the case of siRNA, generally it is the 3'-end of sense strand. The synthesis of 3'-end modified RNA requiring lipophilic, long chain ligands or chromophores, using 3'→5' synthesis methodology is challenging, requires corresponding solid support and generally results in low coupling efficiency and lower purity of the final oligonucleotide, in general, because of the large amount of truncated sequences containing desired hydrophobic modification.

The present inventors have approached this problem by developing reverse RNA monomer phosphoramidites for RNA synthesis in 5'→3'-direction. This arrangement leads to very clean oligonucleotide synthesis allowing for introduction of various modifications at the 3'-end cleanly and efficiently. In order to enhance stability and eliciting of additional favorable biochemical properties, this technique can utilize 2'-5'-linked DNA (Structure 5) and RNA (Structure 6) which have been developed in the past.

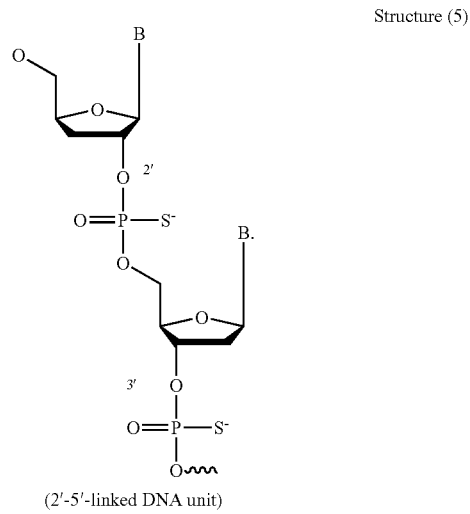

Structure (5)

(2'-5'-linked DNA unit)

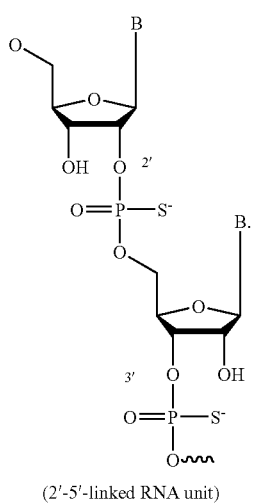

Structure (6)

(2'-5'-linked RNA unit)

For the efficient delivery of RNA and to increase cellular concentration of oligonucleotides, lipids containing oligonucleotides are generally synthesized, since lipids containing synthetic nucleosides enhance uptake of many synthetic nucleoside drugs, like AZT. Lipipoid nucleic acids are expected to reduce the hydrophilicity of oligonucleotides. Similarly hydrophobic molecules such as cholesterol can bind to LDL particles and lipoproteins, and activate a delivery process involving these proteins to transport oligonucleotides. It has also been shown that lipidoic nucleic acids improve the efficacy of oligonucleotides. Shea, R. G., Marsters, J. C., Bischofberger, N., Nucleic Acids Res., 18, 3777, 1990; Letsinger, R. L., Zhang, G., Sun, D. K., Ikeuchi, T., Sarin, P. S., Proc. Natl. Acad. Sci. USA 86, 6553, 1989; Oberhauser, B., and Wagner, E., Nucleic Acids Res., 20, 533, 1992; Saison,-Behmoaras, T., Tocque, B., Rey, I., Chassignol, M., Thuong, N. T., Helene, C. The EMBO Journal, 10, 1111, 1991; Reed, M. W., Adams, A. D., Nelson, J. S., Meye R. B., Jr., Bioconjugate Chem., 2, 217, 1991; Polushin, N. N., Cohen, J., J. Nucleic Acids Res., 22, 5492, 1994; Vu, H., Murphy, M., Riegel, Joyce, M., Jayaraman, K., Nucleosides & Nucleotides, 12, 853, 1993; Marasco, Jr., Angelino, N. J., Paul, B., Dolnick, B. J., Tetrahedron Lett., 35, 3029, 1994. In the studies, the Tm of a series of hydrophobic groups, such as adamantane (structure 7), eicosenoic acid (structure 8), and cholesterol were attached to oligodeoxy nucleotide sequences at the 3'-end and were hybridized to complementary RNA sequences; the Tm was found to be unaffected, which indicates that such groups do not intererefere with oligo hybridization properties; Manoharan, M., Tivel, K. L., Andrade, L. K., Cook, P. D., Tetrahedron Lett., 36, 1995; Manoharan, M., Tivel, K. L., Cook, P. D., Tetrahedron Lett., 36, 3651-3654, 1995; Gerlt, J. A. Nucleases, 2 nd Edition, Linn, S. M., Lloyd, R. S., Roberts, R. J., Eds. Cold Spring Harbor Laboratory Press, p-10, 1993.

Structure 7

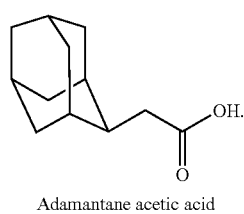

Adamantane acetic acid

Structure 8

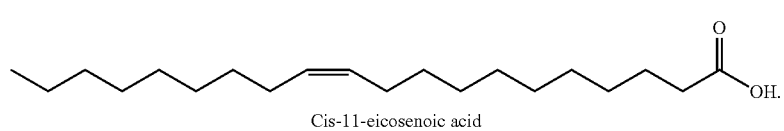

Cis-11-eicosenoic acid

Structure 9

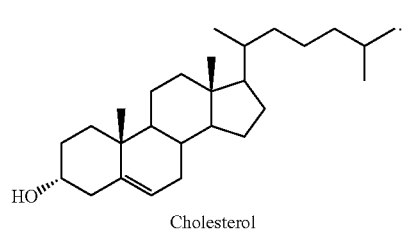

Cholesterol

Structure 10

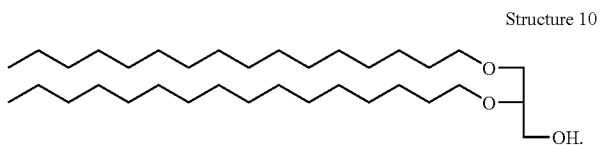

2,3-Di hexadexyl-rac-glycerol

Besides the preceeding lipidoic molecules other class of molecules, which have shown high promise are short and long chain polyethyene glycols (PEG), Bonora, G. M., Burcovich, B., Veronese, F. M., Plyasunova, O., Pokrovsky, A. and Zarytova, V., XII International Round Table Conference, Nucleosides, Nucleotides and their Biological Applications, La Jolla, Calif., September, 15-19, PPI 89, 1996. For efficient delivery of synthetic RNA, and DNA molecules PEG attachment to various oligonucleotides have shown to very favorable properties. PEG-oligomers have shown nice enzymatic stability by preventing fast digestion. The thermal melting behaviour was not affected, thereby still retaining properties of double strand formation.

The approach of the present inventors to produce reversed RNA phosphoramidites required selective introduction of 5'-esters, such as 5'-benzouyl, acetyl, levulinyl or substituted-5'-benzoyl-n-protected ribonucleoside. Subsequent introduction of an appropriate protecting group at 2'-position, such as 2'-tBDsilyl or 2'-TOM (triisopropyl silyl methoxy; TOM) was required. In their scheme they show synthesis of selected molecules to achieve this purpose.

In order to produce target compounds, structures (16a-e), the key intermediate required was 2'-silylether-5'-O acylated-N-protected ribonucleoside, compounds (23a-e). The first intermediate required for this was 5'-acylated-N-protected ribonucleoside compound (22a-e). To the best of our knowledge, the compounds (21a-e) have not been reported. The compounds, which are reported for RNA synthesis in the past utilized intermediates, structure 11, 12 and 13. Various 2' and 3' acetates with 5'-acetate; viz., 5'-benzoyl protected nucleosides; Reese, B. E., Jarman, M., Reese, C. B., Tetrahedron, 24, 639, 1968; Neilson, T., Werstiuk, E. S., Can. J. Chem. 49, 493, 1971; Neilon, T., Wastrodowski, E. V., Werstiuk, E. S., Can. J. Chem., 51, 1068, 1973; Eckstein, F., Cramer, F., Chem. Ber., 98, 995, 1965; Zemlicka, J., Chladek, S., Tet. Lett., 3057, 1965, Amarnath, V. & Broom, A. D., Chemical Reviews, 77, 183-219,1977. The present invention, however, required free 2' and 3' hydroxyl groups, such as in structures (22a-e).

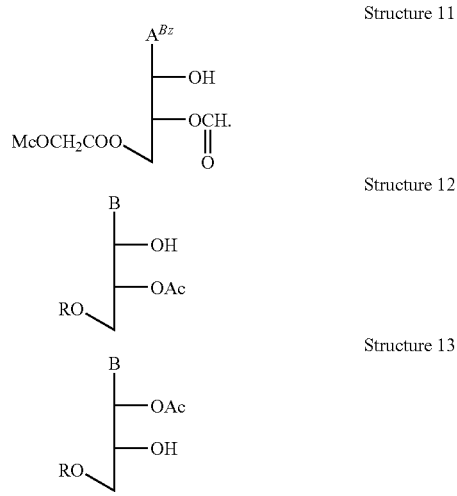

In the present invention, comparative synthesis and purification of RNA's were carried out, both by conventional method (3'→5') and reverse Direction (5'→3'). Observed were: High Purity of RNAs, Smooth 3'-Conjugation-Cholesterol, HEG and PEG (Polyethylene glycols) & Demonstration of Absence of M+1 in Reverse RNA Synthesis The details of synthesis scheme are outlined in the Scheme (2). The 2',3'-Isopropylidene function is utilized to protect the 2',3' hydroxyl groups of ribose of n-protected ribonucleosides. A number of preferred n-protecting groups are shown in the Scheme (2). The 5'-hydroxyl group is subsequently protected, preferably with benzoyl group to obtain compounds of general structure 21. The isopropylidene group is then selectively removed under mild acidic conditions well known in the art. This step leads to compounds of general formula 22. Subsequent reaction with TBDM Silyl chloride (tert-butyl dimethyl silyl chloride) leads to mono silyl compound of general formula 23. The present inventors have observed that 3'-TBDMS group, i.e., the formation of compound structure 24 is not preferred in this process. In most of the cases they observed a clean product whose structure was confirmed to be 23 by chemical and analytical methods.

Purification is carried out at each step either via crystallization or column chromatography at each of the steps of the process mentioned above. Subsequent reaction with dimethoxytrityl chloride (DMT-chloride) in pyridine leads to 3'-DMT-2'-TBDMS-n-protected nucleosides of the general structure 26. Each of the compounds were fully purified by column chromatography.

Altough they utilized TBDMS group to produce 2'-TBDMS ether, other silyl ethers can be utilized at this step. A careful aqueous/methanolic NaOH hydrolysis resulted in compounds with free 5'-hydroxyl group, general structure 27.

Selective 5'-benzoyl removal with aqueous or methanolic base is well known in the art. The compounds 3'-DMT-2'-TBDMS-n-protected nucleosides (structure 27) were purified by silica gel column chromatography. The purified compounds (structure 27) were subsequently phosphorylated with phosphorylating reagents, such as n,n-diisopropylamino cyanoethyl phosphonamidic chloride or 2-cyanoethyl,n,n,n,n-tetraisopropyl phosphane to yield the corresponding phosphramidites (structures 16). Both the phosphorylating reagents, n,n-diisopropylamino cyanoethyl phosphonamidic chloride or 2-cyanoethyl, n,n,n,n-tetraisopropyl phosphane are readily available in the market[1], and the methods of phosphorylation to produce corresponding phosphoramidites are well known in the art.

[1] Manufactured by ChemGenes Corp.

SUMMARY OF THE INVENTION

The present invention provides novel RNA monomer phosphoramidites shown below in Structure (14). The synthetic route that has been developed allows obtaining desired phosphoramidites without contamination from unwanted isomers.

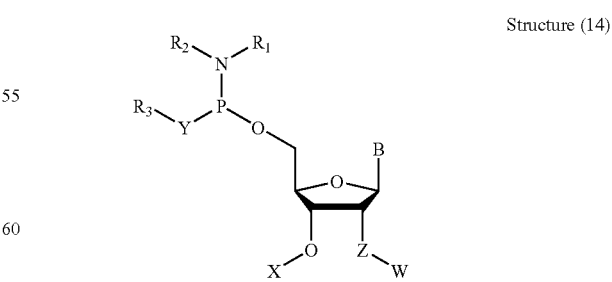

The RNA phosphoramidite monomers in this invention contain 3'-DMT group in ribonucleosides, carrying 5'-cyanoethylphosphoramidite (CED) and various methyloxy or silyl protecting groups at 2'-position of the ribose moiety (Structure 14). The solid support has protected RNA nucleosides containing 3'-DMT group and 5' terminus is attached to solid support (Structure 15).

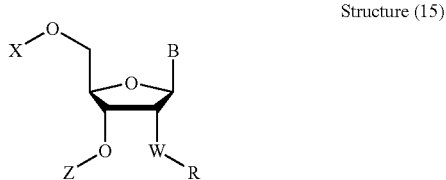

Structure (15)

The RNA phosphoramidites can be used in the reverse, 5'→3'-directed oligonucleotide synthesis. A large number of RNA synthesis, Conventional (3'→5') and Reverse Direction (5'→3') were performed as part of the experimentation.

The modification or labeling at 3'-terminus of RNA oligomer can be attached by using corresponding phosphoramidite or active ester at the end of the synthesis and do not require special solid support. Moreover, the approach of this invention leads to a very clean 3'-labeled oligonucleotide and expensive methods of purification are not required.

High Purity levels of RNAs were consistently obtained in the RNA synthesis by Reverse Direction (5'→3'), resulting in Smooth 3'-Conjugation of molecules such as Cholesterol, HEG (hexaethyloxyglycol) and PEG (Polyethylene glycols). It was also further demonstrated that in the RNA synthesis in the reverse Direction (5'→3'), there is absence of M+1 oligonucleotide impurities.

Salient Features of the processes of the present invention, from the discussion, experimental data and the drawing FIGS. 9-18, described herebelow, include the following observations:

I. The crude RNA's have much closer impurities (N-1) in the conventional method (3'-5'-direction), as compared to reverse RNA synthesis (5'-3' direction). Therefore after purification RNA synthesized by reverse RNA synthesis are purer.

II The feature mentioned above is much more visible in the synthesis of cholesterol attached to 3'-end of RNA (see FIG. 11 vs. FIG. 12). Therefore it is easier to purify RNA with cholesterol at 3'-end synthesized by reverse RNA synthesis (see FIG. 12).

III. M+1 impurities are essentially absent in the RNA's synthesized by reverse RNA synthesis method.

It is postulated that in the molecule, ribonucleoside-3'-DMT-2'-tBDsilyl-5'-phosphoramidites, the 3'-DMT is not cleaved by 5-ethylthiotetrazole or similar activators during oligonucleotide coupling step and within the coupling time of oligonucleotide chain extension.

IV. RNA containing macromolecules at the 3'-end which are generally inaccessible by conventional methods (3'→5') are easily synthesized by reverse RNA synthesis (5'→3' direction). These RNA's can be produced in high purity.

V. 3'-PEG RNA (21-mer) was synthesized, and after purification was essentially 100% pure (see FIGS. 16, 17 and 18).

observed at 969.4; calculated; 970.18.

Figure 1:
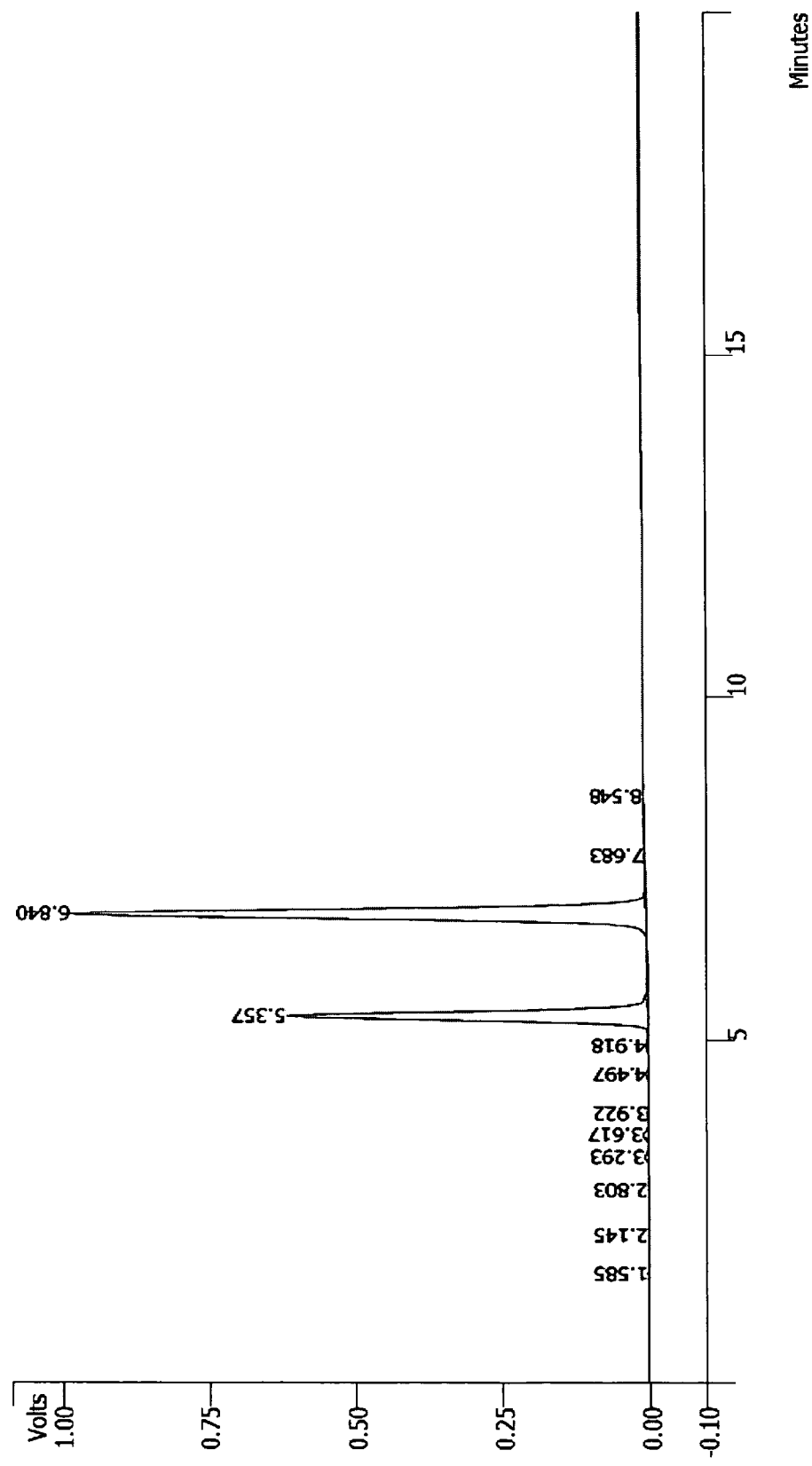
FIG. 1. HPLC-Chromatogram of $N^4$-Benzoyl-2'O-TBDMS-3'-O-DMT-adenosine-5'-cyanoethyl-N,N-diisopropyl-phosphoramidite (16a), 98.6% purity.
Figure 2:
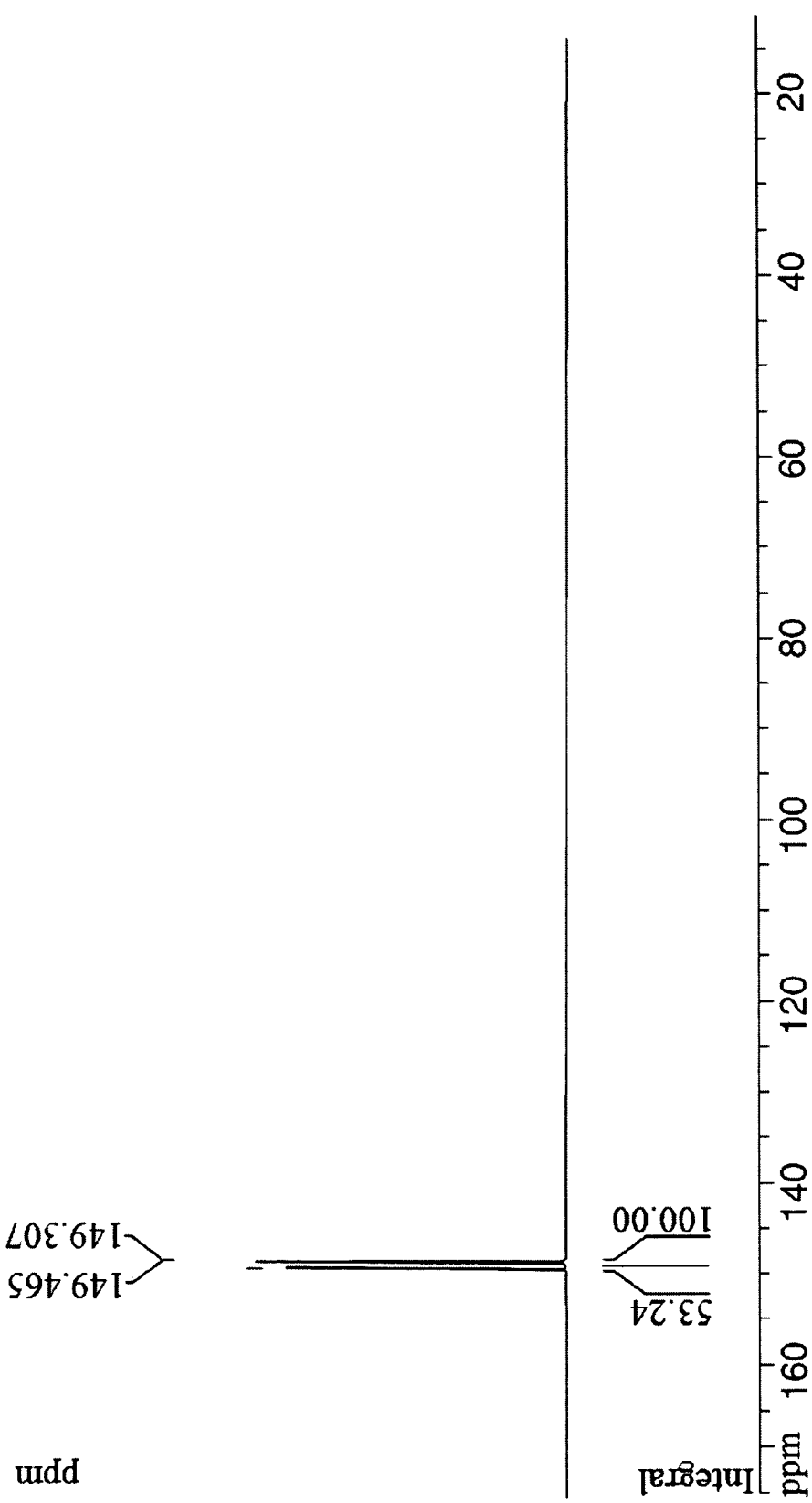
FIG. 2. NMR $^{31}$P Spectrum of $N^4$-Benzoyl-2'O-TBDMS-3'-O-DMT-adenosine-5'-cyanoethyl-N,N-diisopropyl-phosphoramidite (16a), sharp doublet at 149.465 ppm & 149.307 ppm; delta;0.158, 98.6% purity.
Figure 3:
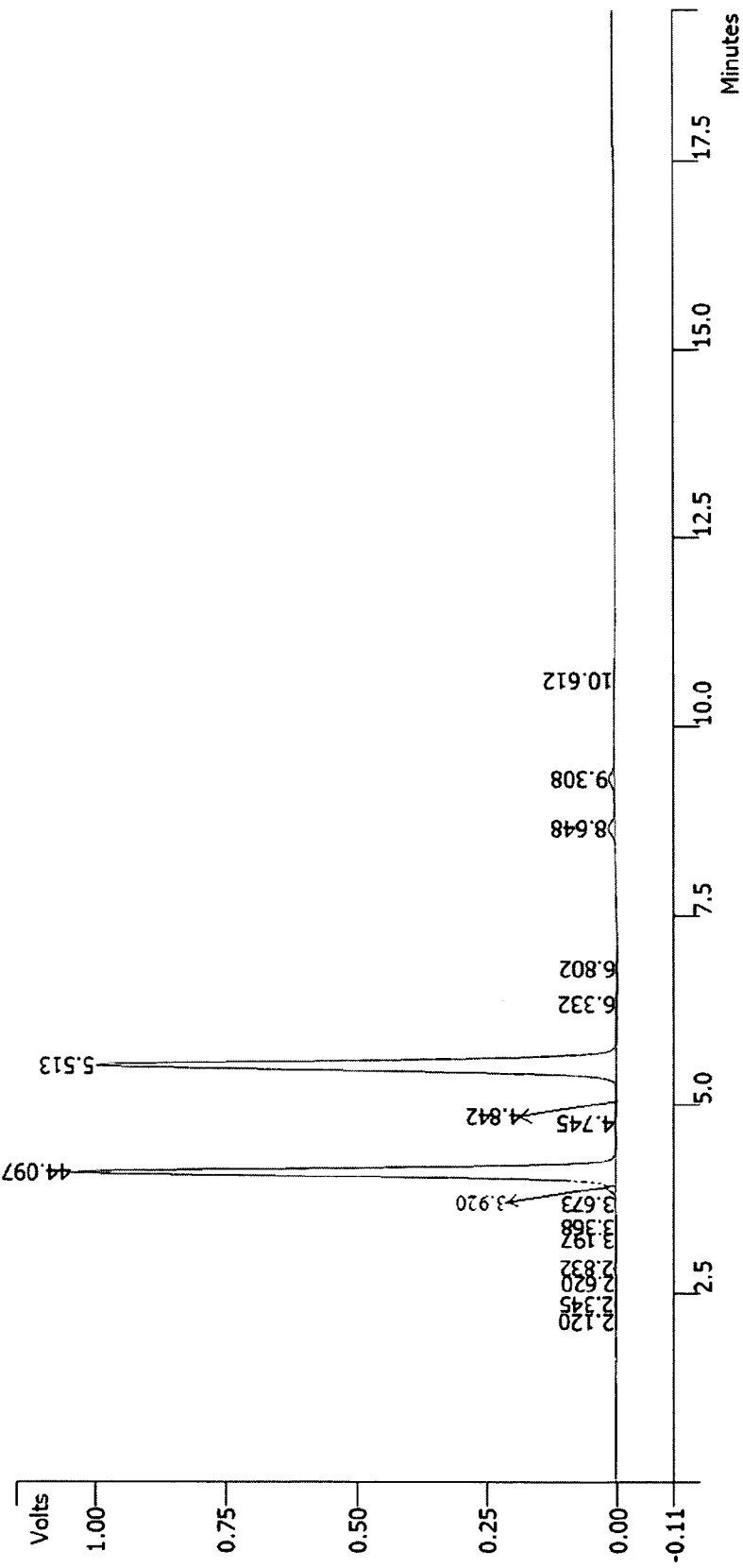
FIG. 3. HPLC-Chromatogram of $N^4$-Acetyl-2'-O-TBDMS-3'-O-DMT-cytidine-5'-cyanoethyl-N,N-diisopropyl-phosphoramidite (16c), 96.9% purity.
Figure 4:
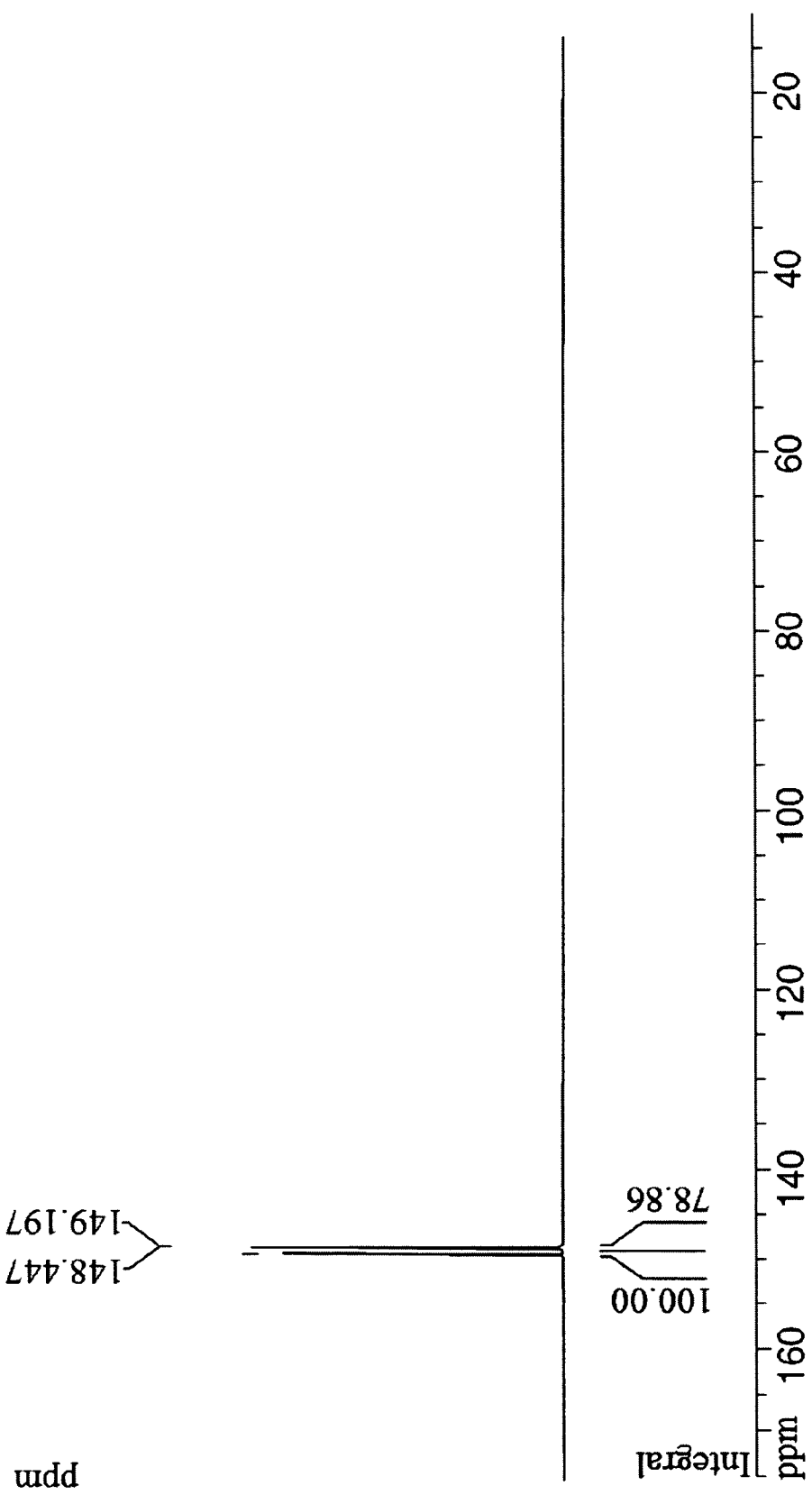
FIG. 4. NMR $^{31}$P Spectrum of $N^4$-Acetyl-2'-O-TBDMS-3'-O-DMT-cytidine-5'-cyanoethyl-N,N-diisopropyl-phosphoramidite (16c), sharp doublet at 149.447 ppm & 149.197 ppp; delta;0.250,100% purity.
Figure 5:
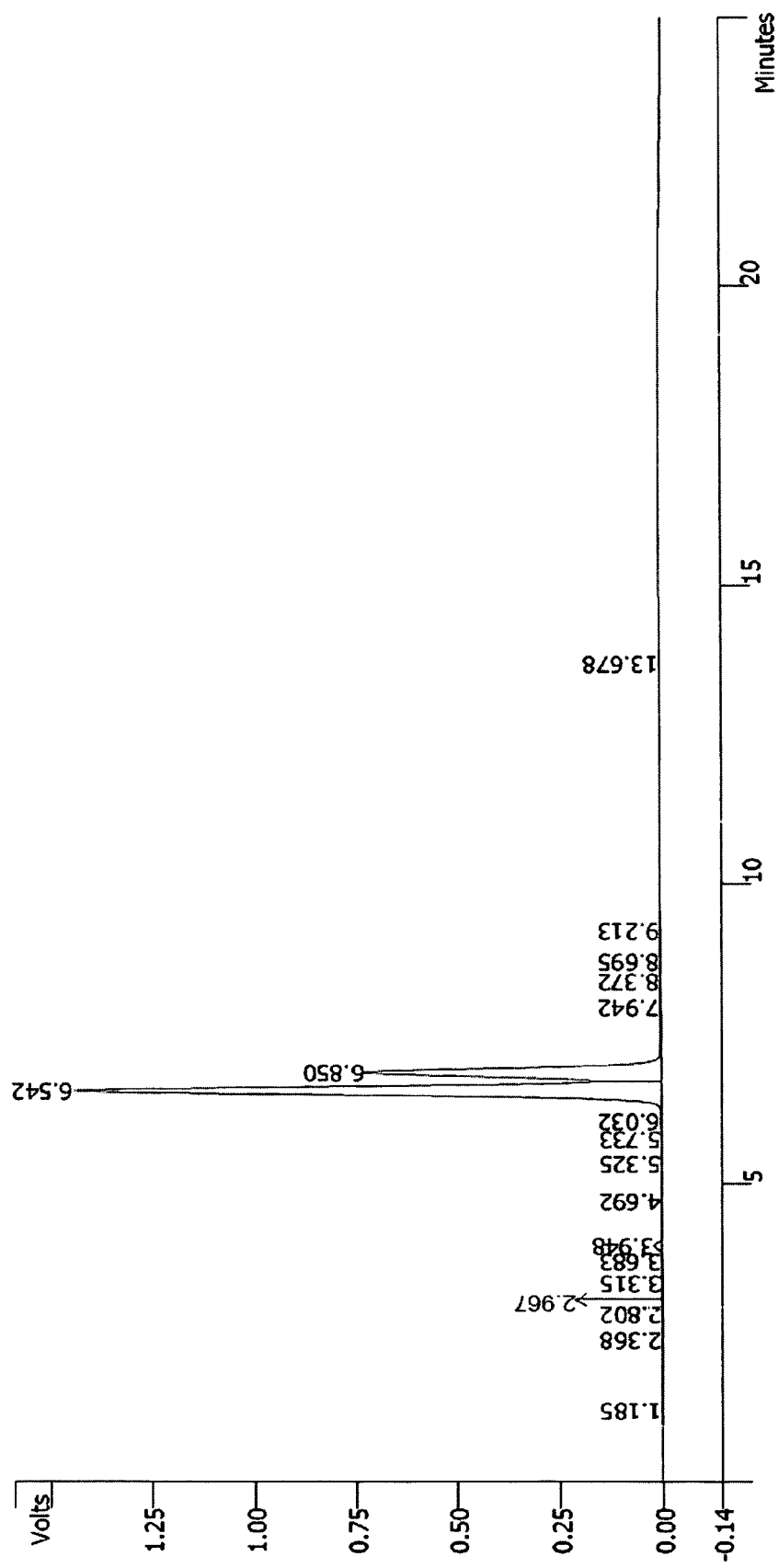
FIG. 5. HPLC-Chromatogram of $N^2$-Isobutyryl-2'-O-TBDMS-3'-O-DMT-guanosine-5'-cyanoethyl-N,N-diisopropyl-phosphoramidite (16d), 98.3% purity.
Figure 6:
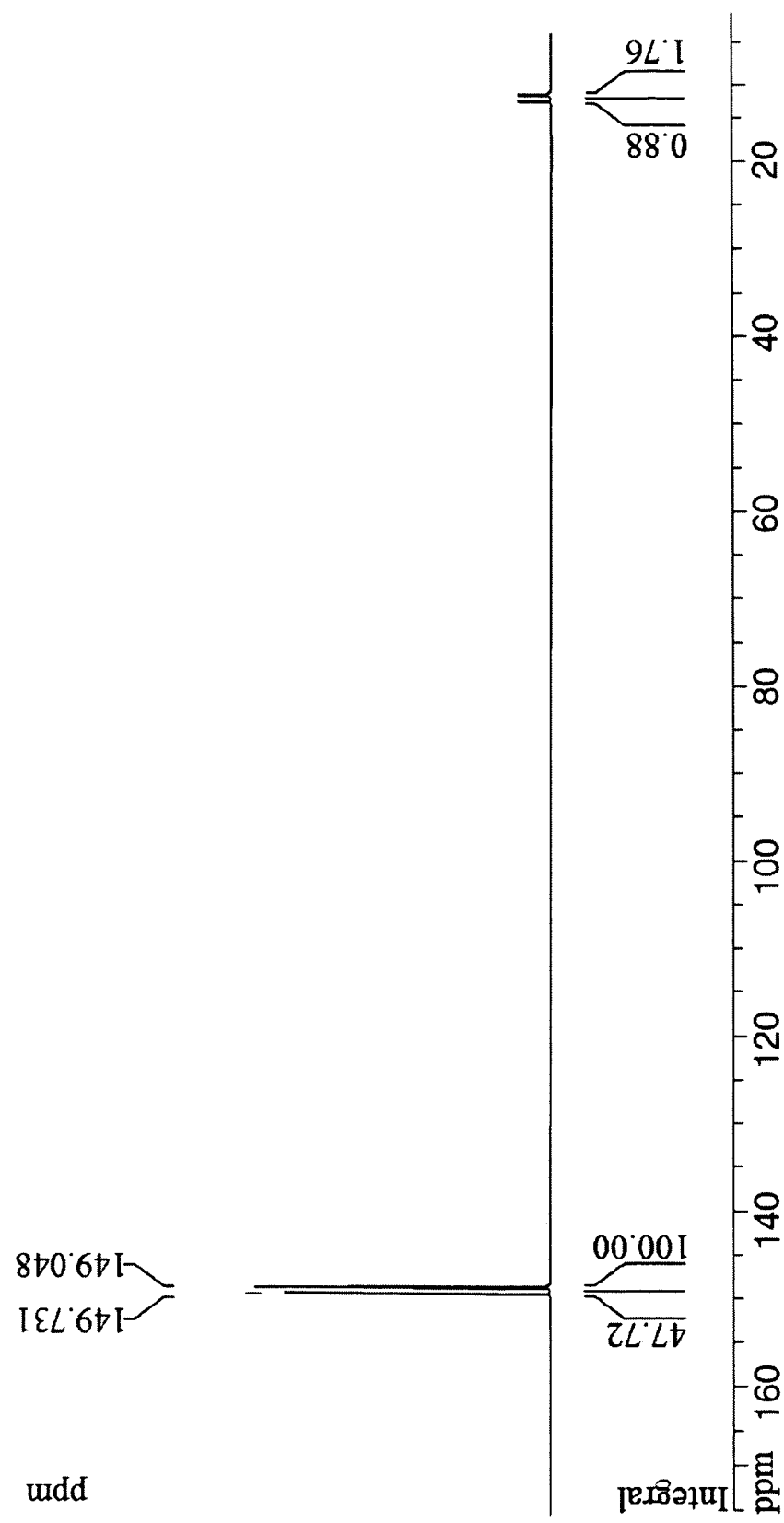
FIG. 6. NMR $^{31}$P Spectrum of $N^2$-Isobutyryl-2'-O-TBDMS-3'-O-DMT-guanosine-5'-cyanoethyl-N,N-diisopropyl-phosphoramidite (16d), sharp doublet at 149.731 ppm & 149.048ppm, delta;0.683, 100% purity.
Figure 6A:
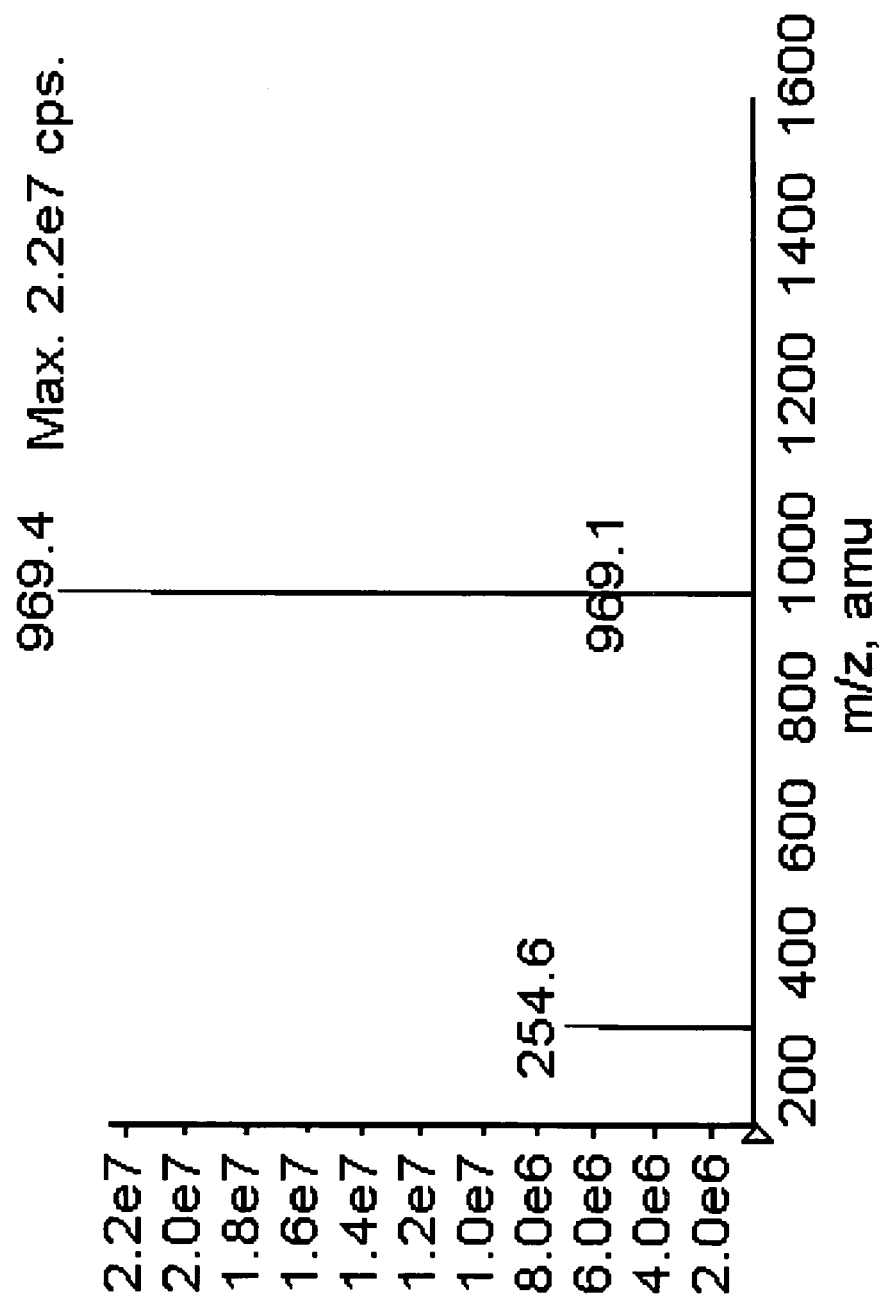
FIG. 6a. Mass Spectrum of the compound (16 d); $N^2$-Isobutyryl-2'-O-TBDMS-3'-O-DMT guanosine-5'-cyanoethyl-N,N-diisopropyl-phosphoramidite, Negative ion mass.
Figure 6B:
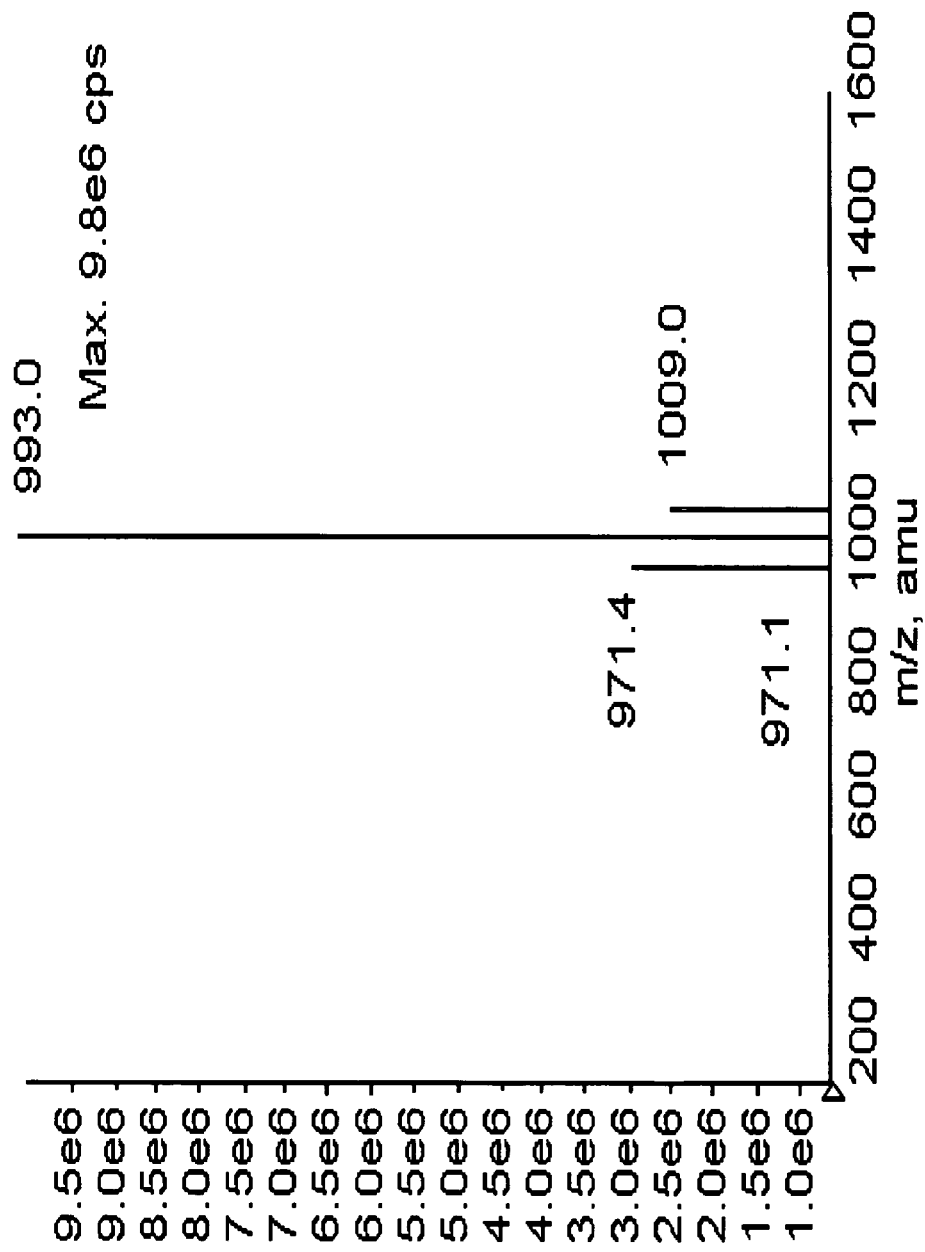

FIG. 6b. Mass Spectrum of the compound (16 d); $N^2$-Isobutyryl-2'-O-TBDMS-3'-O-DMT-guanosine-5'-cyanoel-N, N-diisopropyl-phosphoramidi, Positive ion mass;

observed at 993.0; calculated ; 993.18 (+Na).

Figure 7:
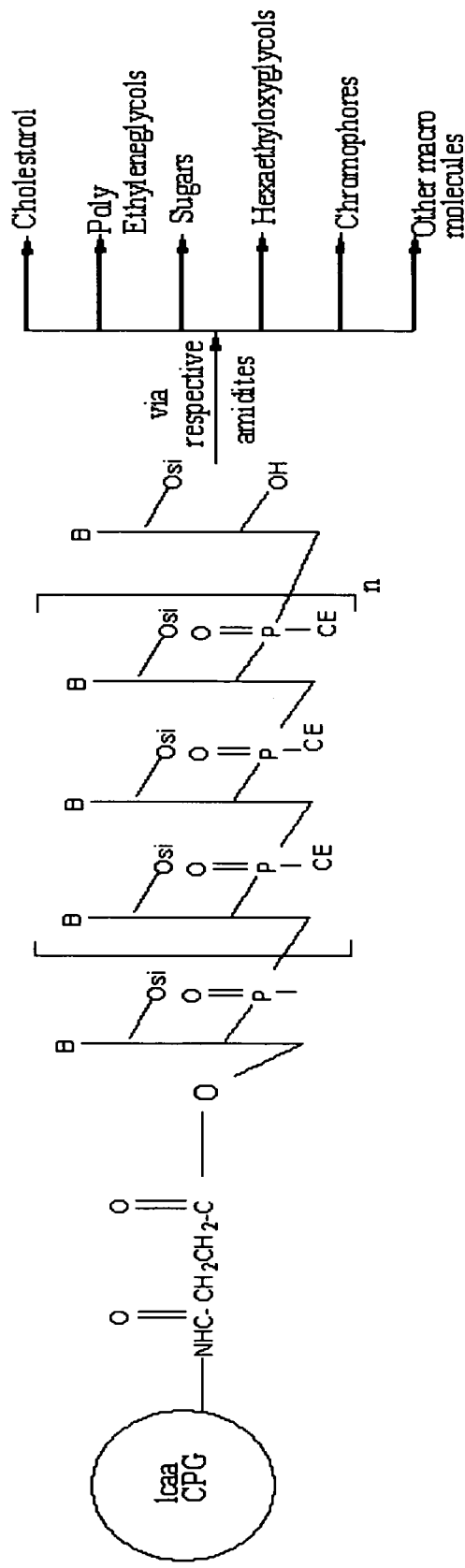

FIG. 7. Diagrammatic representation of 5'→3' RNA synthesis and application to 3'-modifications.

Figure 8:
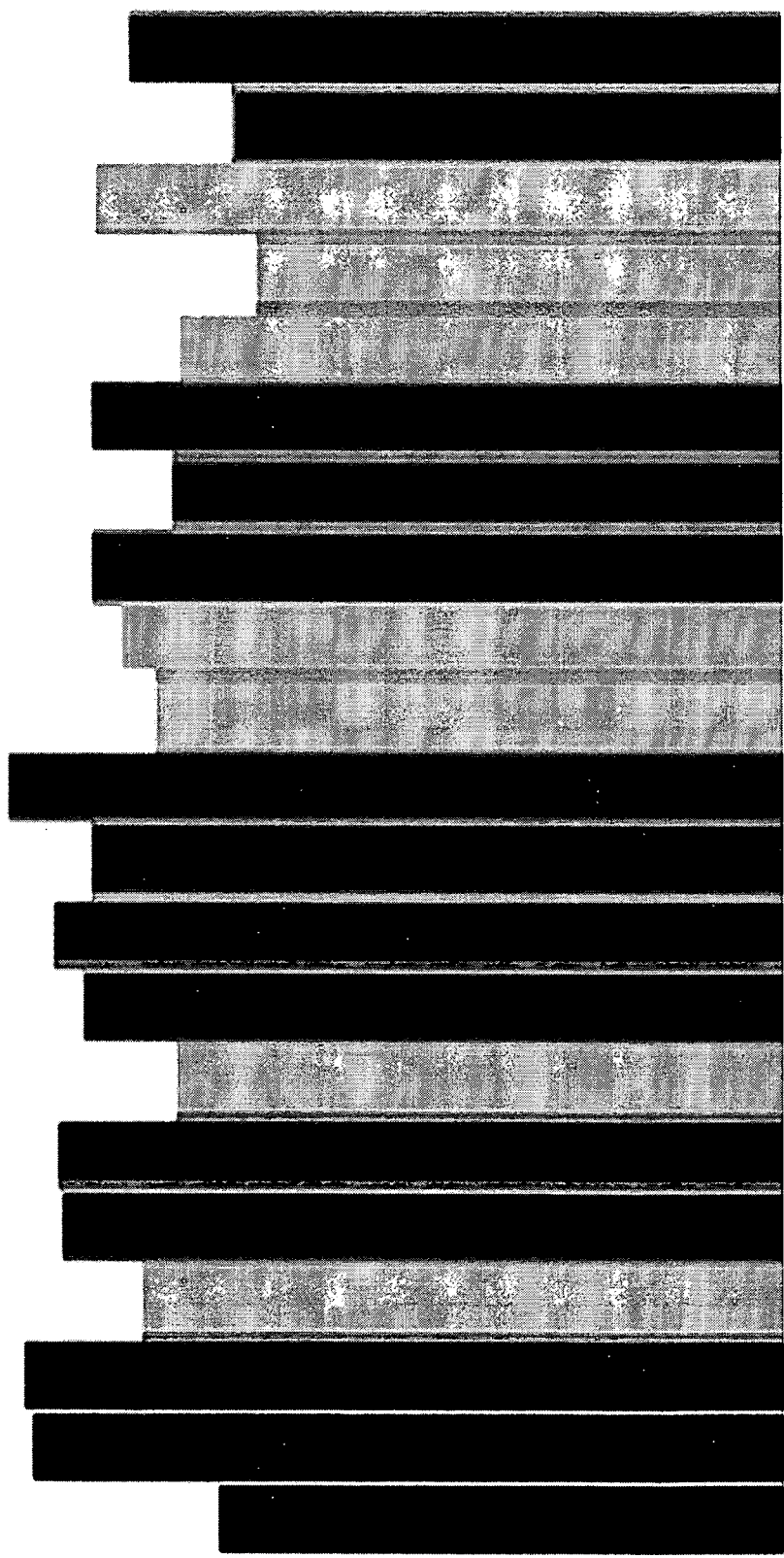

FIG. 8. Coupling Efficiency Trityl Histogram Notes (21 mer RNA synthesis):

Coupling Efficiency (step wise yield by base leveling) : 99.6%

Final Yield (by rolling average): 100% ; Stepwise Yield for monomer G: 100%

Stepwise Yield for monomer A: 99.2% ; Stepwise Yield for monomer C: 99.6%

Stepwise Yield for monomer C: 99.6% ; Stepwise Yield for monomer U :100.0%

Figure 9A:
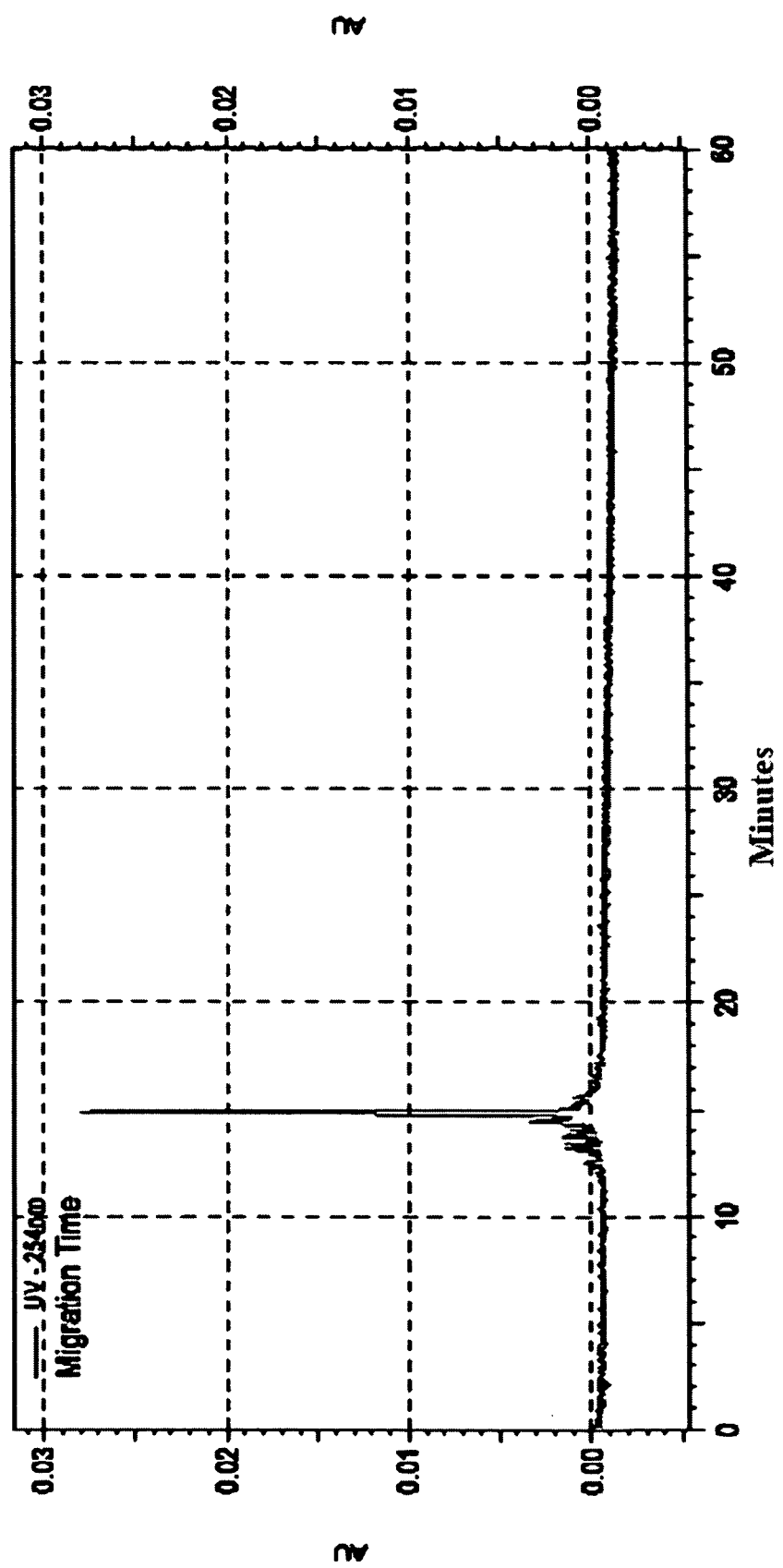

FIG. 9a. Electropherogram of the crude oligonucleotide SEQ ID No 1 made by conventional method (3'→5' direction).

Figure 9:
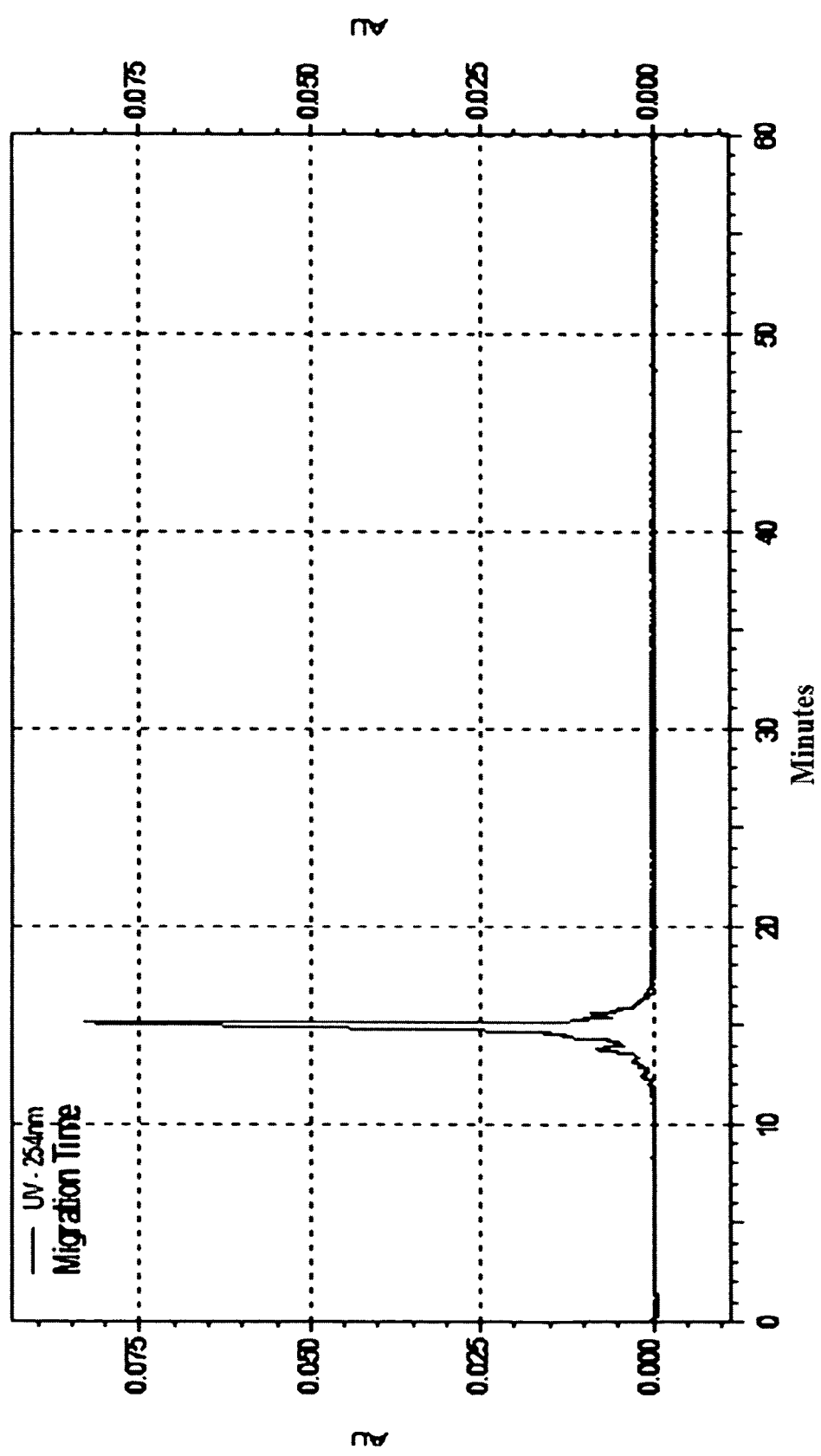

FIG. 9. Electropherogram of the purified oligonucleotide SEQ ID No 1 made by the conventional method (3'→5' direction). Expedite Model 8909-1 umole scale. Crude purity; 90.78%.

Figure 10:
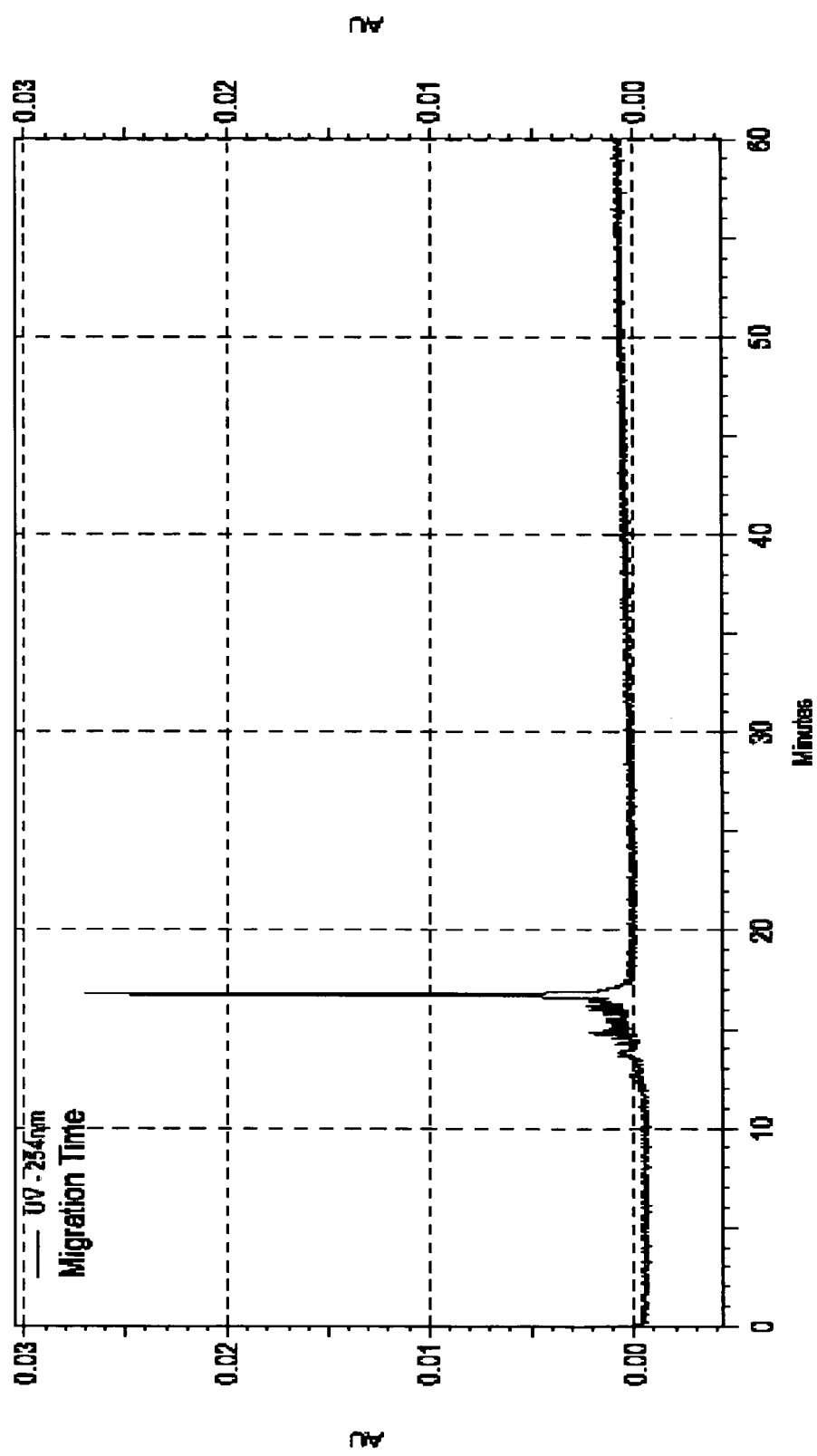

FIG. 10. Electropherogram of the crude 21-mer RNA made by Reverse RNA synthesis (5'→3' direction). Expedite Model 8909-1 umole scale. Crude purity; 78.55.

Note: M+1 seems to be non-existent in the reverse synthesis.

Figure 11:
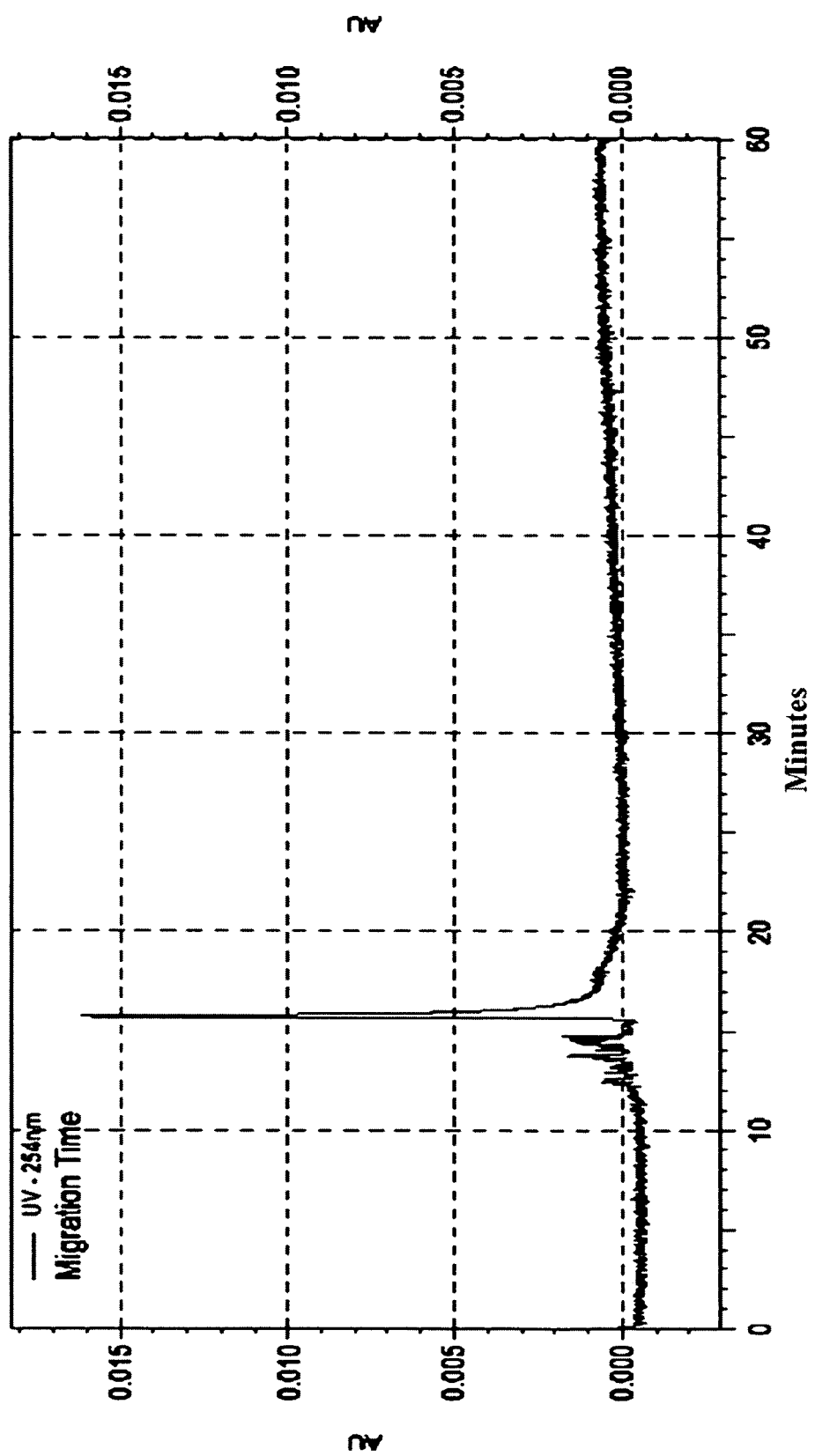

FIG. 11. Electropherogram of the crude oligonucleotide SEQ ID No 2 made by conventional method. Crude 21-mer RNA with 3'-cholesterol CPG, made by conventional method (3'→5' direction). Expedite Model 8909-1 umole scale. Crude purity; 82.83%.

Note: The humps present at right side, most likely due to M+1 species.

Figure 12:
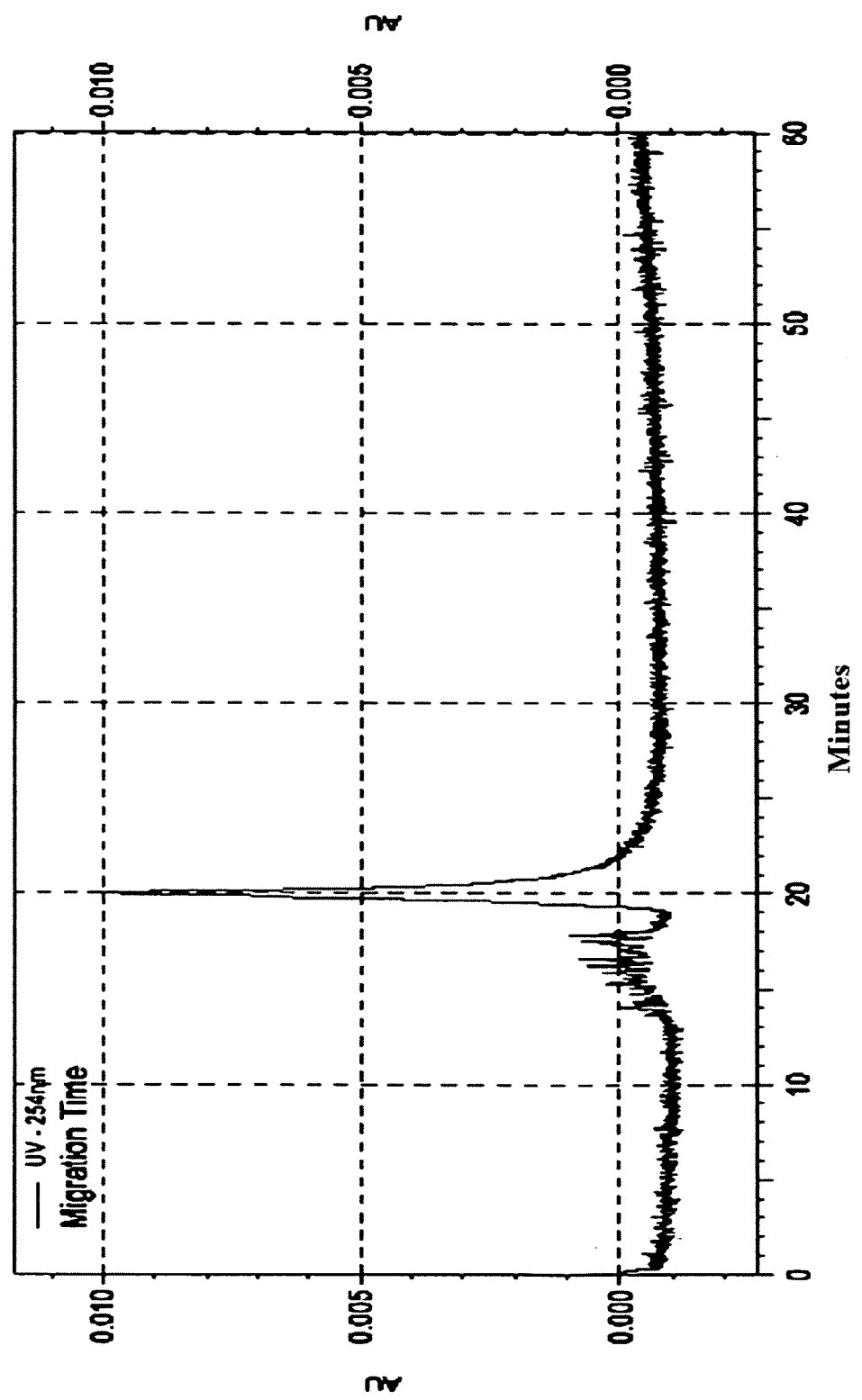

FIG. 12. Electropherogram of the crude oligonucleotide SEQ ID No 2 made by Reverse RNA synthesis (5'Δ3' direction). Expedite Model 8909-1 umole scale. Crude purity; 85.76%. Note: M+1 seems to be non-existent in the reverse synthesis.

Figure 13:
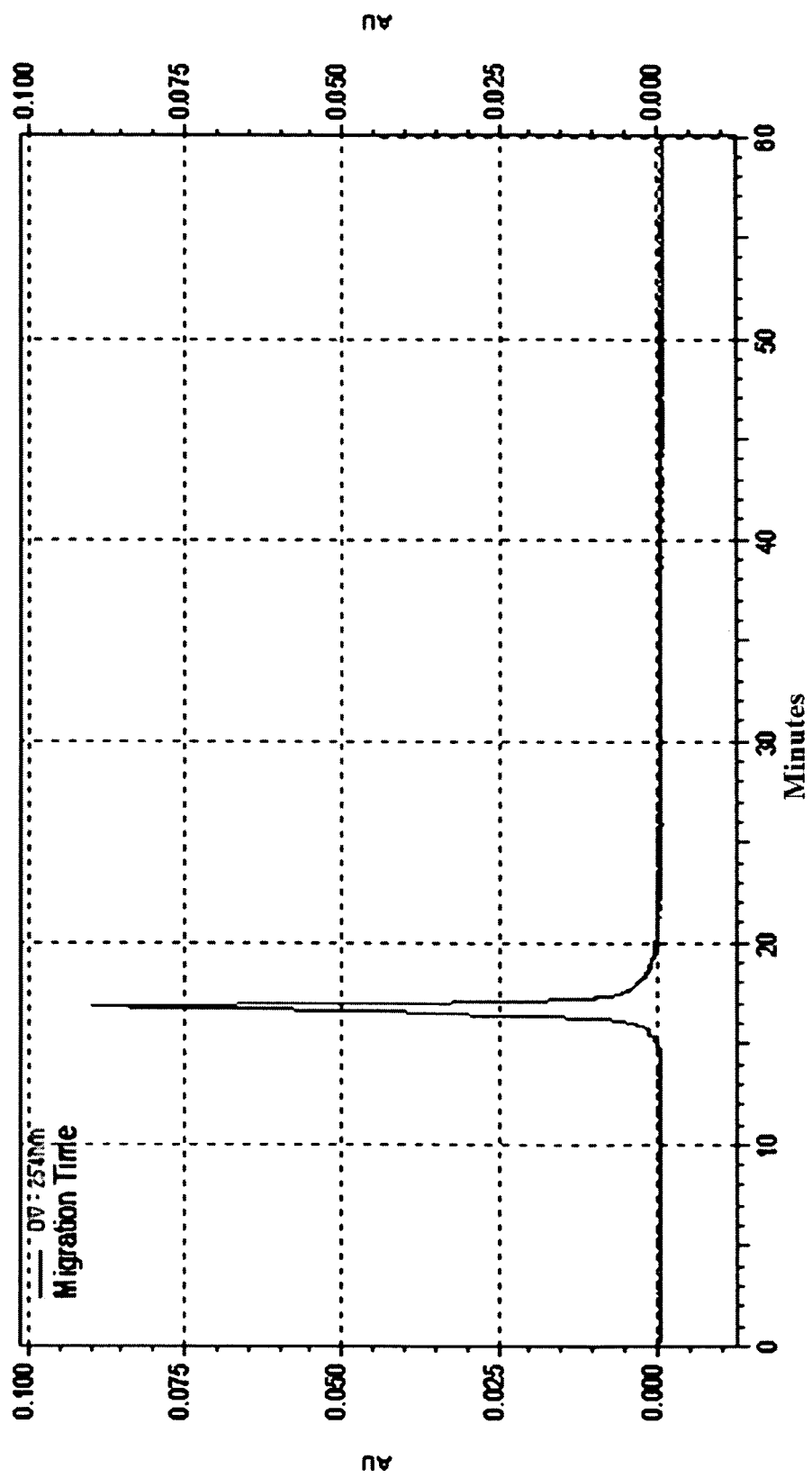

FIG. 13. 21-Mer RNA with 3'-Cholesterol-TEG linker. Reverse direction (5'→3') synthesis and HPLC purification. 1 umole scale. Purity; 99.9%.

Figure 14:
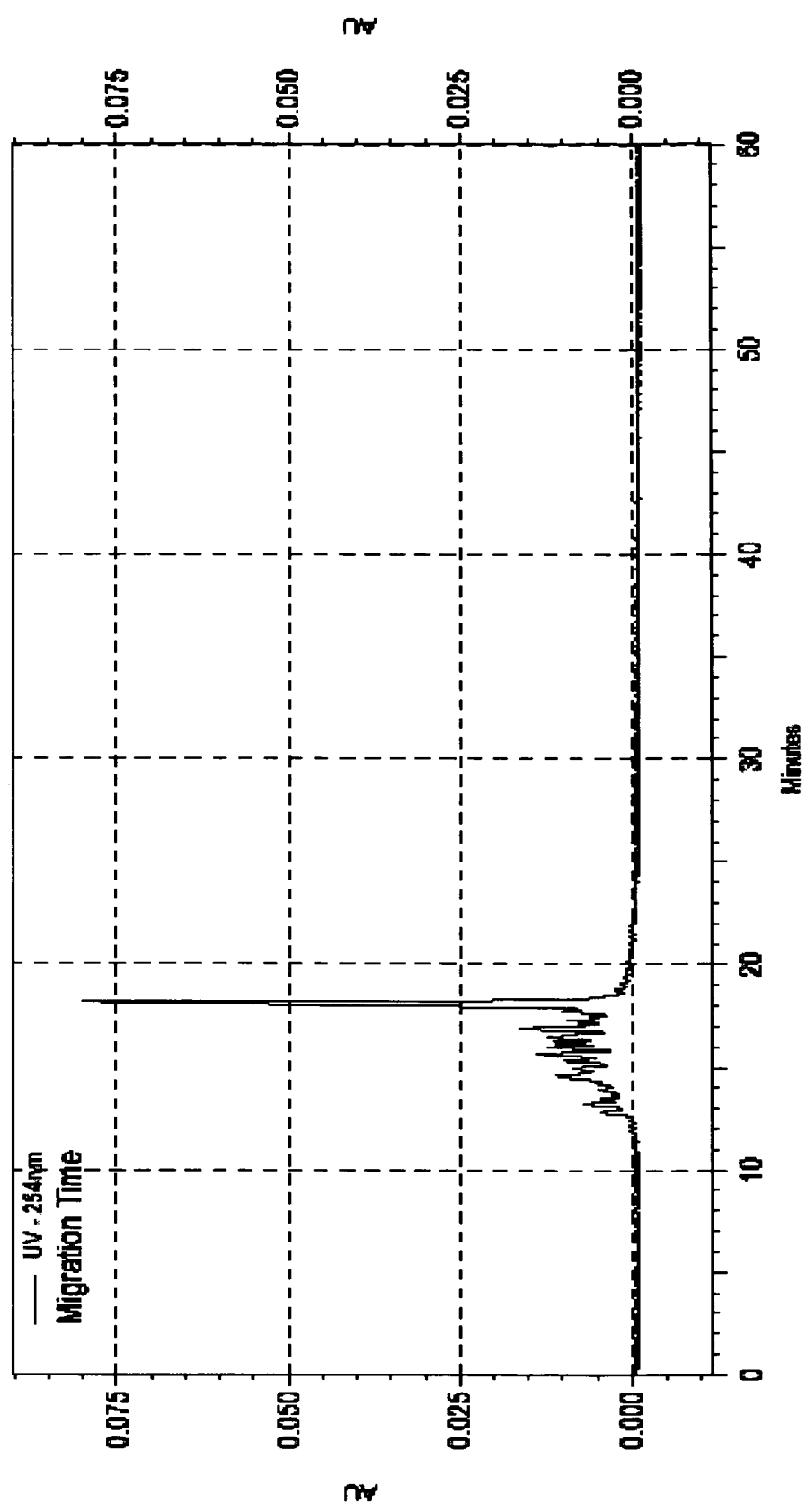

FIG. 14. Electropherogram of the crude oligonucleotide SEQ ID No 4 made by reverse RNA synthesis. Crude purity; 56.60%.

Figure 15:
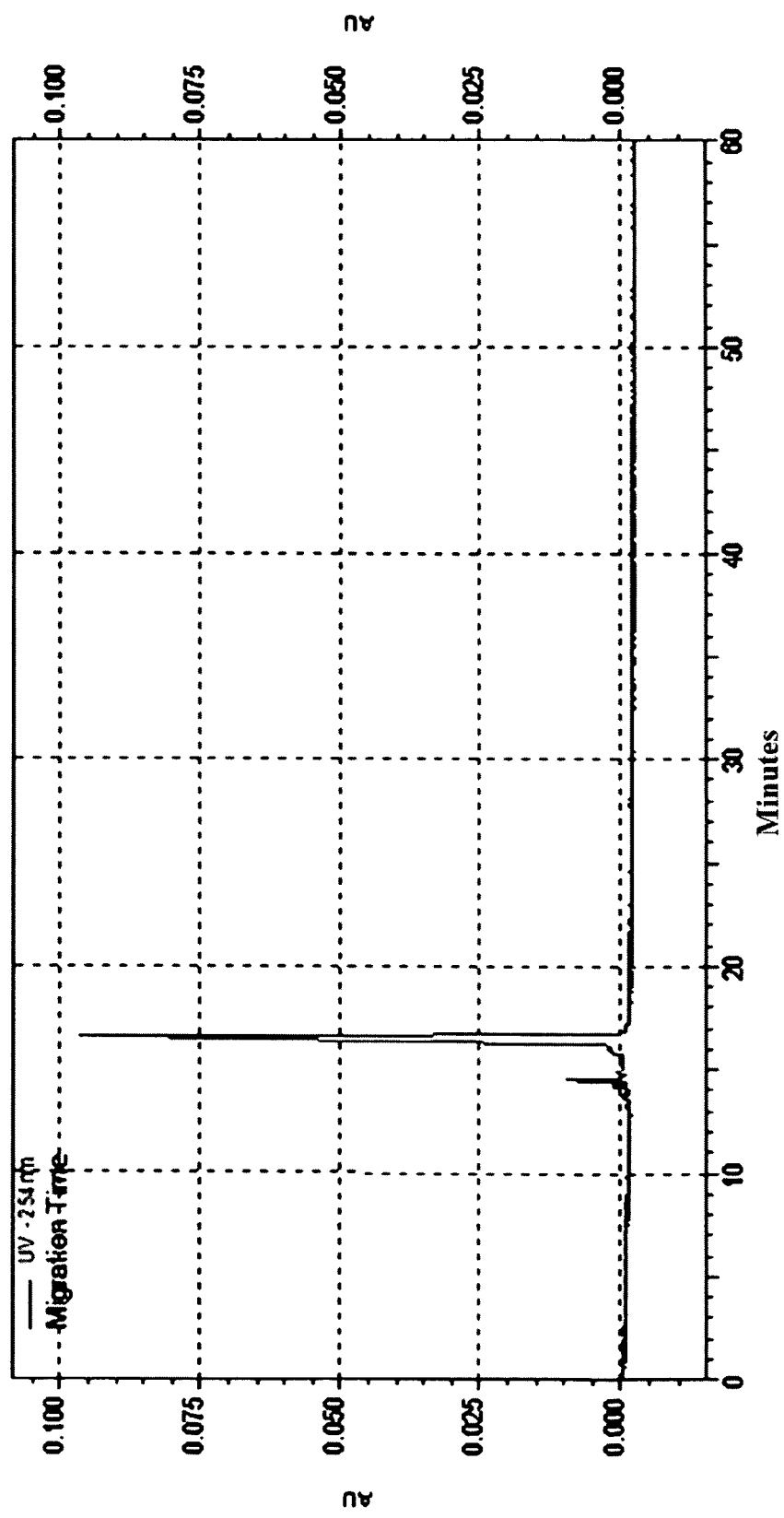

FIG. 15. 21-Mer RNA synthesized by reverse direction (5'→3'), followed by HEG (Hexa-ethyloxyglycol) attachment. After HPLC purification, Purity; 94.39%.

Figure 16:
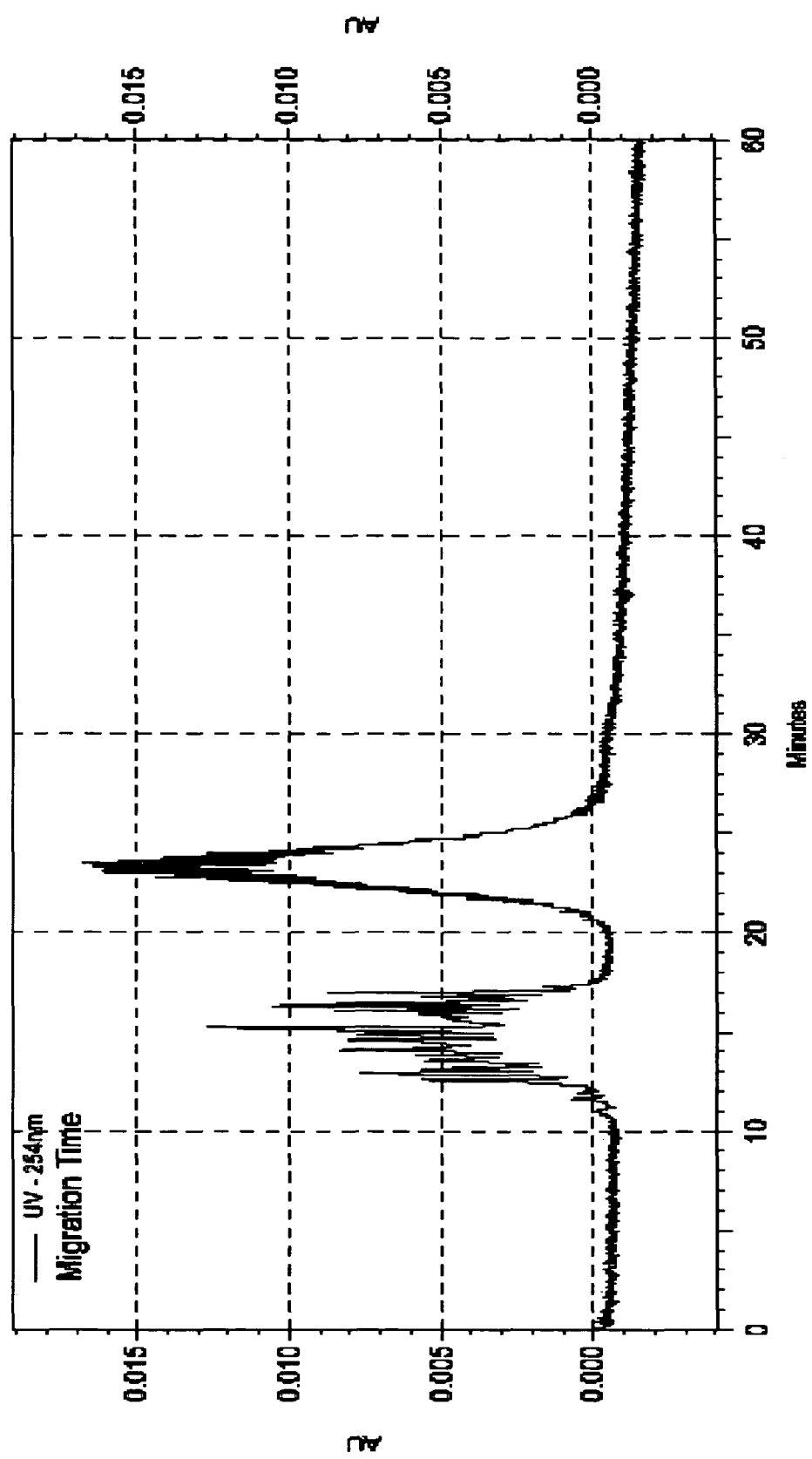

FIG. 16. Electropherogram of the crude oligonucleotide SEQ ID No 3 made by reverse synthesis. 21-mer RNA synthesis with 3'-PEG (Polyethyleneglycol; MW; 2000). Expedite model 8909-1 umole scale synthesis. Crude purity; 91.87%. Cleanly separated broad peak present.

Figure 17:
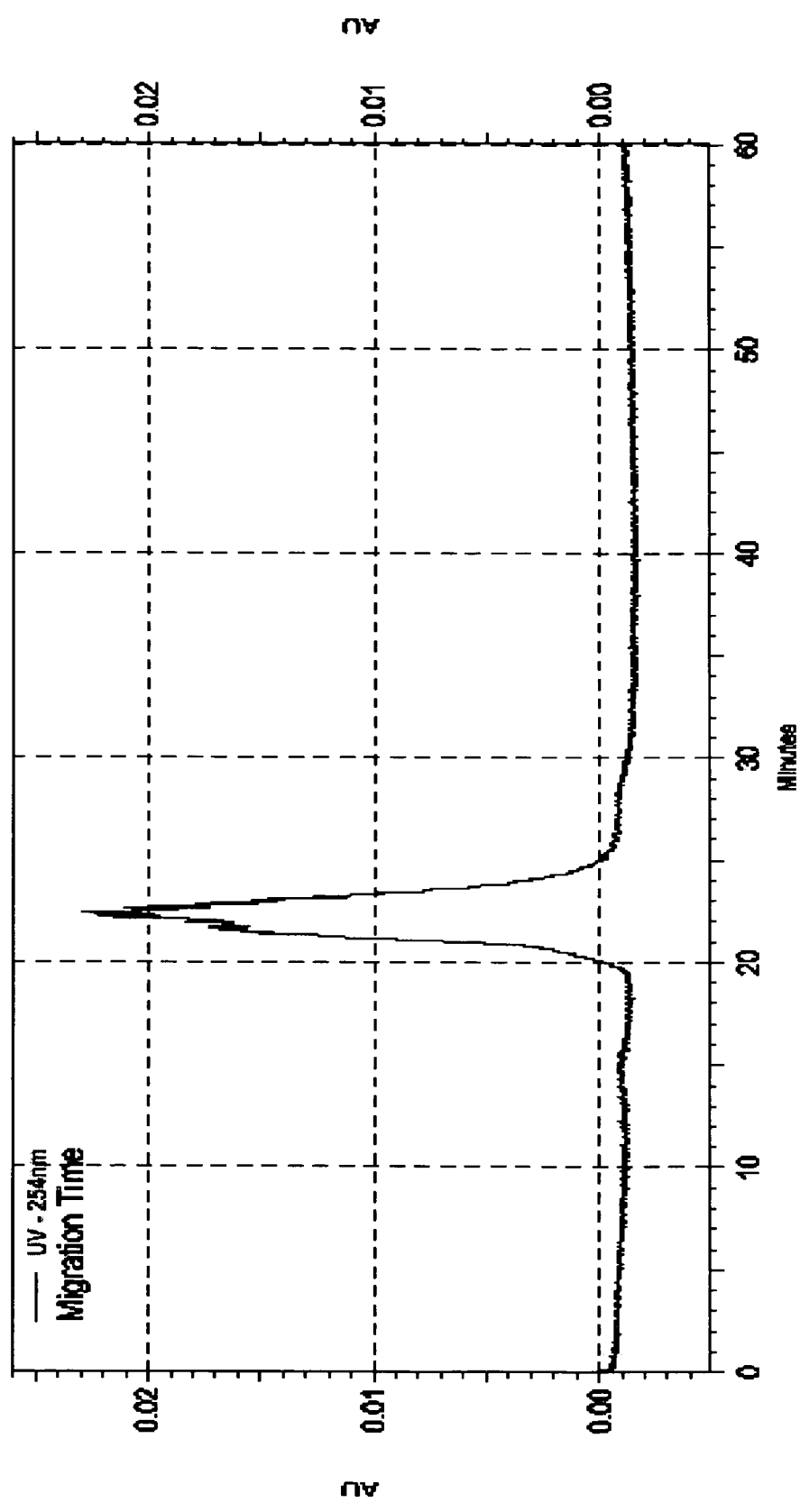

FIG. 17. Electropherogram of the oligonucleotide SEQ ID No 4 made by reverse synthesis. 21-mer RNA synthesis with 3'-PEG (Polyethyleneglycol; MW; 2000). Expedite model 8909-1 umole scale synthesis. Reverse phase HPLC Purified; Purity; 100%.

Figure 18:
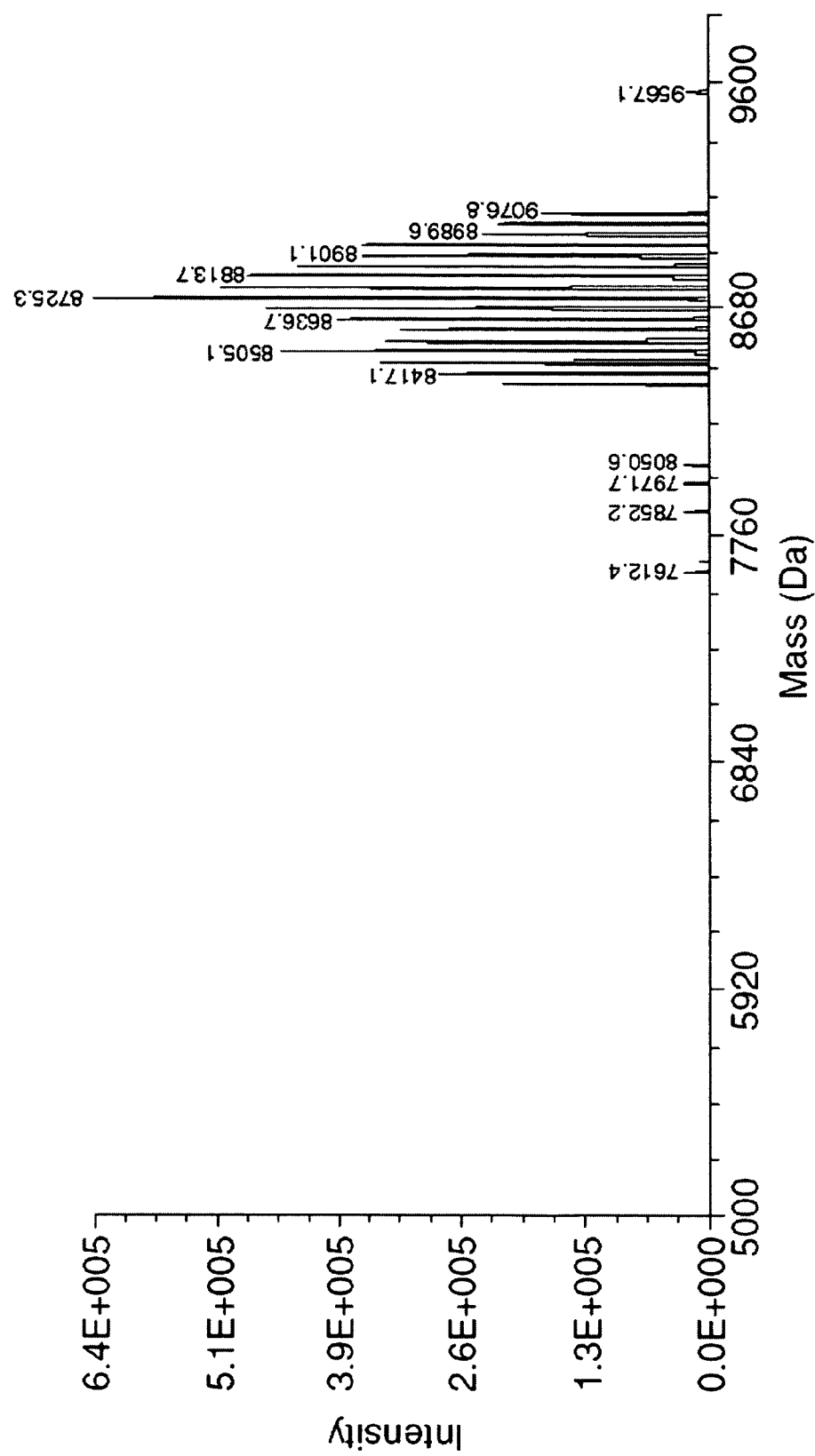

FIG. 18. ESI Mass Spectral analysis of 21-mer RNA with 3'-PEG-2000 attachment, purified RNA as shown in FIG. 17. The synthesis was carried out in reverse direction (5'→3' direction). The PEG-2000 was attached as last step via the corresponding phosphoramidite, ChemGenes catalog; CLP-3119 Calculated Molecular Weight: 8684.1 Observed Molecular Weight: 8681.1 Note: There is a distribution of at least 14 PEG species of the RNA on both sides of the Calculated molecular weight with PEG-2000. Thus species from 8417.1 to 8945.3 are present with a molecular weight difference of a glycol unit (+/−44).

DETAILED DESCRIPTION OF THE INVENTION

The reverse RNA monomer phosphoramidites in the present invention carry a 3'-DMT group in ribonucleosides, carrying 2'-tBDsilyl (tBDSi)-5'-cyanoethylphosphoramidite (CED) (Structure 16), 3'-DMT-2'-tBDsilyl-5'-succinyl-Icaa CPG-n-protected nucleosides (Structure 17) or 3'-DMT-2'-triisopropylsiloloxymethyl (TOM)-5'-CED phosphoramidite group (Structure 18).

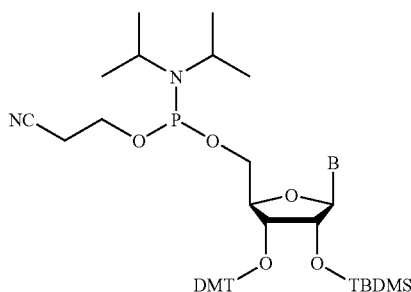

Where B=A (N-Bz), C (N-Bz), C (N-Ac), G (N-iBu), A (N-tBPac), C (N-tBPac), C (N-tBPac), G (N-tBPac), A (N-Pac), C (N-Pac), C (N-Pac), G (N-Pac), U.

Structure (16). 3'-DMT-2'-tBDSilyl-5'-Amidites (Reverse RNA-tBDsilyl-amidites)

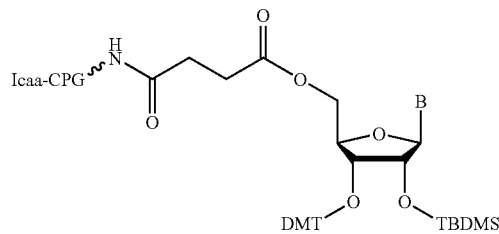

Where B=A (N-Bz), C (N-Bz), C (N-Ac), G (N-iBu), A (N-tBPac), C (N-tBPac), C (N-tBPac), G (N-tBPac), A (N-Pac), C (N-Pac), C (N-Pac), G (N-Pac), U.

Structure (17). 3'-DMT-2'-tBDSilyl-5'-CPG (Reverse RNA-tBDsilyl-5'-Icaa CPG)

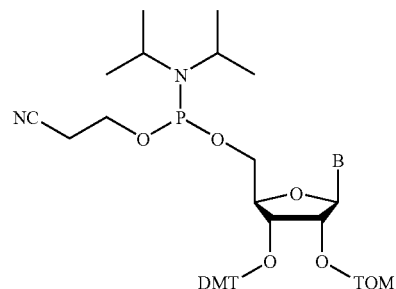

Where B=A (N-Ac), C (N-Ac), G (N-Ac), U.

Structure (18). 3'-DMT-2'-TOM (triisopropylsilyl oxymethylene)-5'-amidites (Reverse RNA-TOM-5'-amidites)

The invention also teaches the method for preparing the disclosed compositions. The starting base protected nucleoside 19 affording isopropyliden protected nucleoside 20. Benzoylation followed by isopropyliden group removal yields 5'-benzolylated nucleoside 22. Consecutive silylation reaction with TBDMS chloride in pyridine provides mixture of 2'- and 3'-TBDMS protected nucleosides (23 and 24) in the ratio of 3:2 respectively. After column chromatography isomers have been resolved and isolated in % yield. Further reaction of the isomer 23 afforded 3'-DMT-2'-TBDMS protected nucleoside 26.

It is therefore conceivable that during subsequent functionalization of 3'-hydroxyl group, there will be significant migration of 2'-tBdsilyl group.

Scheme (1)

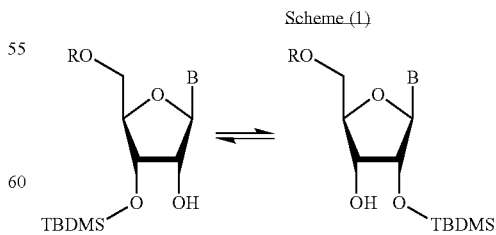

During the functionalization of 3'-hydroxyl group with DMT-(4,4-dimethoxytrityl), no significant migration was observed to occur. Moreover, the 3'-TBDMS protected isomer 24 contamination of the 2'-TBDMS protected nucleoside 23 with its isomer 24, unwanted isomer 25 cannot be formed in the tritylation conditions and desired nucleoside 26 can be isolated in high purity. The 3'-TBDMS protected nucleoside 24 can be utilized in the synthesis of the desired product and converted into 23 due to isomerization process outlined in the scheme 1.

Removal of 5'-benzoyl group with sodium hydroxide in methanol followed by phosphitilation reaction using CEDP and DIPA tetrazolate affords the final reverse phosphoramidite 16.

3'-DMT-5'-CED phosphoramidites indicated per step coupling surpassing 99%, leading to high purity RNA. A large number of homopolymers and 20-21 mers oligonucleotides have been synthesized using these monomer phosphoramidfites. The typical data is presented in the FIG. (8).

Our data show that there is no difference in coupling efficiency during oligo synthesis using the reverse RNA monomers (for 5'→3'-direction) as compared to standard 3'-CED phosphoramidites in synthesis in 3'→5' direction (see FIGS. 9 and 10).

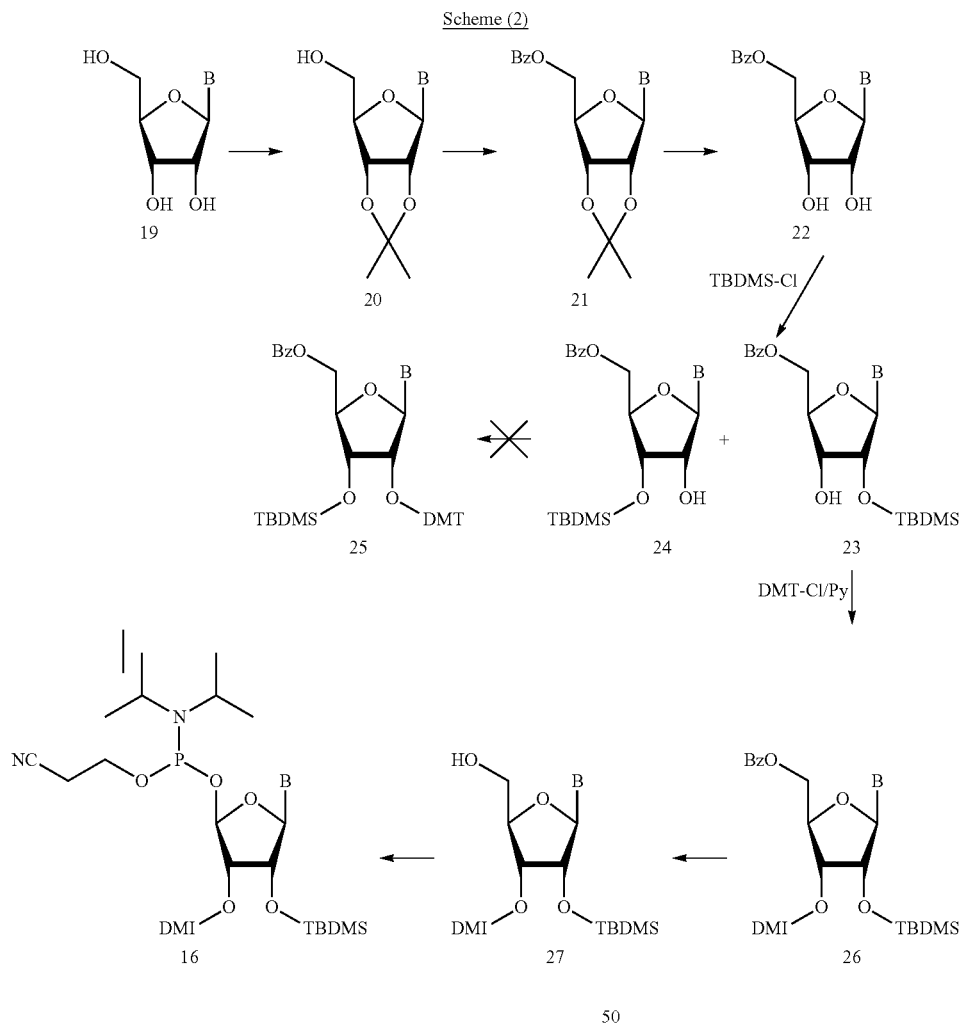

Where B=a) A (N-Bz), b) C (N-Bz), c) C (N-Ac), d) G (N-iBu) e) A (N-tBPac), f) C (N-tBPac), g) G (N-tBPac), h) A (N-Pac), i) C (N-Pac), j) G (N-Pac), k) U.

Oligonucleotide synthesis using reverse phosphoramidites was performed in the direction from 5'→3'.

The examples provided below further illustrate the invention; these are illustrative only and should not be construed as in any way limiting the scope of the invention. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents. All oligonucleotide sequences are written from the 5'-terminus on the left to the 3'-terminus on the right. The coupling efficiency of the In another embodiment the invention provides method for synthesis of ribonucleic acid oligomers with modification or labeling of 3'-end of an oligonucleotide. The synthesis of 3'-end modified RNA requiring lipophilic, long chain ligands or chromophores fluorophores and quenchers can be performed using corresponding phosphoramidites. Our data, as captured in FIGS. 11 and 12, show that 5'→3'-direction synthesis has very distinct advantage compared to conventional method.

In addition, the 3'-modifications that not available on solid support such as HEG or PEG-2000 can be easily introduced by using 5'→3'-direction synthesis and purified by reverse-phase HPLC. The oligonucleotide SEQ ID No 4 has been purified by RP HPLC affording 95-98% pure products (see FIG. 15).

EXPERIMENTAL: EXAMPLES

Example 1

Synthesis of $N^2$-Isobutyryl-2'-O-TBDMS-3'-O-DMT-guanosine-5'-cyanoethyl-N,N-diisopropyl-phosphoramidite (16d) as shown in the scheme 2

$N^2$-Isobutyryl-2'-O-TBDMS-3'-O-DMT-5'-O-benzoyl-guanosine (26d): To the solution of 4 g (7.0 mmol) of the compound 23d in 60 mL of pyridine were added 9.5 g (28.0 mmol) of DMT chloride in one portion at room temperature for 48 hrs. Reaction mixture was quenched with 2 mL of cold methanol then half of the solvent was removed under diminished pressure, mixed with 20 mL of chloroform, washed with 50 mL of saturate sodium bicarbonate and 50 mL of brine. Organic layer was separated and dryed over anhydrous $Na_2SO_4$. Flash chromatography with 5:2:3 chloroform/hexanes/acetone provided 1.7 g (27.8%) of the compound 26d. TLC system: 5:2:3 chloroform/hexanes/acetone, Rf=0.42. ESMS 896.1 $[C_{48}H_{55}N_5O_9Si (M+Na)^+$ requires 896.1].

$N^2$-Isobutyryl-2'-O-TBDMS-3'-O-DMT-guanosine (27d): To the solution of 14 g (16.0 mmol) of the compound 26d in 196 mL of pyridine and 21 mL of methanol mixture were added 16 mL of 2 M aqueous solution of sodium hydroxide (32.0 mmol) dropwise with stirring at 0-5° C. during the course of 25 min. The reaction mixture was neutralized with 15 mL of 2 M HCl. The solvent was removed under diminished pressure and residue was extracted with two portions of 25 mL of chloroform. Organic layer was combined, washed with 50 mL of brine and dried over anhydrous $Na_2SO_4$. Flash chromatography with 5:2:3 chloroform/hexanes/acetone provided 10.4 g (84.3%) of the compound 27d. $^1H$ NMR ($CDCl_3$/$D_2O$) δ −0.54 (s, 3H), 0.01 (s, 3H), 088 (s, 9H), 1.21 (d, 3H, J=7.0 Hz), 1.23 (d, 3H, J=7.0), 2.66 (qq, 1H, J=7.0), 2.89 (d, 1H, J=12 Hz), 3.28 (s, 1H), 3.37 (dd, 1H, $J_{5a,5b}$=15 Hz, $J_{5,4}$=2.5 Hz) 3.80 (s, 6H), 4.24 (d, 1H, J=5 Hz), Hz), 1.23 (d, 3H, J=7.0), 2.66 (qq, 1H, J=7.0), 2.89 (d, 1H, J=12 Hz), 3.28 (s, 1H), 3.37 (dd, 1H, $J_{5a,5b}$=15 Hz, $J_{5,4}$=2.5 Hz) 3.80 (s, 6H), 4.24 (d, 1H, J=5 Hz), 4.83 (dd, 1H, $J_{2,1}$=8 Hz, $J_{2,3}$=5 Hz), 5.97 (d, 1H, J=8 Hz), 6.84 (dd, 4H, J=9 Hz, J=2 Hz), 7.23 (t, 1H, J=7.5 Hz), 7.30 (t, 2H, J=7 Hz), 7.45 (m, 4H), 7.59 (d, 2H, J=7.5 Hz), 7.77 (s, 1H). ESMS 792.8 $[C_{41}H_{51}N_5O_8Si (M+Na)^+$ requires 792.9].

$N^2$-Isobutyryl-2'-O-TBDMS-3'-O-DMT-guanosine-5'-cyanoethyl-N,N-diisopropyl-phosphoramidite (16d): To the solution of 10.4 g (13.5 mmol) of the compound 27, 3.4 g (26.12 mmol) of ethylthiotetrazole, 4.7 mL (27 mmol) of DIPEA and 1.08 mL (13.5 mmol) of N-methylimidazole in 104 mL of acetonitrile were added 8.4 mL (26.12 mmol) of 2-cyanoethyl-N,N,N,N-tetraisopropylphosphane dropwise with stirring under Ar at room temperature. After 3 hrs the reaction mixture was diluted with 100 mL of ethylacetate and washed with 200 mL of saturated sodium bicarbonate and 200 mL of brine. The organic layer was separated and dried over 2 g of anhydrous $Na_2SO_4$. Flash chromatography with 7:2:1 chloroform/hexanes/triethylamine provided 12 g (92.1%) of the compound 16d. $^{31}P$ NMR ($CDCl_3$) δ 149.05 and 149.73. ESMS 993.3 $[C_{50}H_{68}N_7O_9PSi (M+Na)^+$ requires 993.2].

Example 2

Synthesis of $N^4$-Acetyl-2'-O-TBDMS-3'-O-DMT-cytidine-5'-cyanoethyl-N,N-diisopropyl-phosphoramidite (16c)

$N^4$-Acetyl-2'-O-TBDMS-3'-O-DMT-cytidine (27c): To the solution of 5 g (6.2 mmol) of the compound 26c in 54 mL of pyridine and 6 mL of methanol mixture were added 6.2 mL of 2 M aqueous solution of sodium hydroxide (12.4 mmol) dropwise with stirring at 0-5° C. during the course of 25 min. The reaction mixture was neutralized with 6 mL of 2 M HCl. The solvent was removed under diminished pressure and residue was extracted with two portions of 15 mL of chloroform. Organic layer was combined, washed with 50 mL of brine and dried over anhydrous $Na_2SO_4$. Flash chromatography with 5:2:3 chloroform/hexanes/acetone provided 4 g (91.9%) of the compound 27c. $^1H$ NMR ($CDCl_3$/$D_2O$) δ 0.07 (s, 3H), 0.16 (s, 3H), 0.97 (s, 9H), 2.24 (s, 3H), 3.16 (br.d, 1H, $J_{5a,5b}$=12 Hz), 3.55 (br.d, 1H, $J_{5a,5b}$=12 Hz) 3.79 (s, 6H), 4.08 (t, 1H, J=4.5 Hz), 4.44 (br.s., 1H), 4.78 (br.s., 1H), 5.61 (d, 1H, J=4.1), 6.80 (dd, 4H, J=7 Hz, J=3 Hz), 7.22 (t, 1H, J=7.5 Hz), 7.27 (t, 2H, J=7 Hz), 7.38 (m, 4H), 7.52 (d, 2H, J=7.3 Hz), 8.08 (br.s, 1H). ESMS 724.8 $[C_{38}H_{47}N_3O_8Si (M+Na)^+$ requires 724.3].

$N^4$-Acetyl-2'-O-TBDMS-3'-O-DMT-cytidine-5'-cyanoethyl-N,N-diisopropyl-phosphoramidite (16c): Was prepared analogously to $N^2$-Isobutyryl-2'-O-TBDMS-3'-O-DMT-guanosine-5'-cyanoethyl-N,N-diisopropyl-phosphoramidite (16d). Yield is 62.6%. $^{31}P$ NMR ($CDCl_3$) δ 149.1 and 149.5. ESMS 925.0 $[C_{47}H_{64}N_5O_9PSi (M+Na)^+$ requires 924.4].

Example 3

Synthesis of 2'-O-TBDMS-3'-O-DMT-Uridine-5'-cyanoethyl-N,N-diisopropyl-phosphoramidite (16k)

2'-O-TBDMS-3'-O-DMT-Uridine (27k): To the solution of 30 g (39 3 mmol) of the compound 26k in 450 mL of pyridine and 45 mL of methanol mixture were added 40 mL of 2 M aqueous solution of sodium hydroxide (80.0 mmol) dropwise with stirring at 0-5° C. during the course of 25 min. The reaction mixture was neutralized with 40 mL of 2 M HCl. The solvent was removed under diminished pressure and residue was extracted with two portions of 50 mL of chloroform. Organic layer was combined, washed with 50 mL of brine and dried over anhydrous $Na_2SO_4$. Flash chromatography with 6.5:2:1.5 chloroform/hexanes/acetone provided 24 g (92.5%) of the compound 9k. $^1H$ NMR ($CDCl_3$) δ 0.06 (s, 3H), 0.14 (s, 3H), 0.97 (s, 9H), 2.12 (br.d, 1H, J=4 Hz), 3.16 (br.dd, 1H, $J_{5a,5b}$=12.7 Hz, $J_{5a4}$=7.6 Hz), 3.55 (br.d, 1H, $J_{5a,5b}$=12.7 Hz $J_{5b4}$=4.3 Hz) 3.65-3-64 (m, 1H) 3.79 (s, 6H), 4.07 (t, 1H, J=4.3 Hz), 4.28 (t, 1H, J=4.3 Hz), 5.66 (d, 1H, J=4.9 Hz), 5.69 (d, 1H, J=8.1 Hz), 6.82 (dd, 4H, J=7 Hz, J=3 Hz), 7.22 (t, 1H, J=7.5 Hz), 7.28 (t, 2H, J=7 Hz), 7.38 (d, 4H, J=8.9 Hz), 7.54 (d, 2H, J=8.8 Hz), 7.68 (d, 1H, J=8.2), 8.74 (br.s, 1H). ESMS $[C_{36}H_{44}N_2O_8Si (M+Na)^+$ requires 683.3].

2'-O-TBDMS-3'-O-DMT-Uridine-5'-cyanoethyl-N,N-diisopropyl-phosphoramidite (16k): To the solution of 24.0 g (36.4 mmol) of the compound 27k, 24 mL (182 mmol) of collidine, 2.88 mL of N-methylimidazole in 190 mL of THF were added 16.22 mL (72.8 mmol) of 2-cyanoethyl-N,N,diisopropylphosphonamidic chloride dropwise with stirring under Ar at room temperature. After 1.25 hrs the reaction mixture was diluted with 100 mL of ethylacetate and washed with 200 mL of saturated sodium bicarbonate and 200 mL of brine. The organic layer was separated and dried over 20 g of anhydrous $Na_2SO_4$. Flash chromatography with 5:4:1 ethylacetate/hexanes/triethylamine provided 18 g (80.0%) of the compound 16k. $^{31}P$ NMR ($CDCl_3$) δ 148.9 and 149.6. ESMS 884.1 $[C_{45}H_{61}N_4O_9PSi (M+Na)^+$ requires 884.0].

Example 4

Synthesis of N⁴-Benzoyl-2'-O-TBDMS-3'-O-DMT-adenosine-5'-cyanoethyl-N,N-diisopropyl-phosphoramidite (16a)

N⁴-Benzoyl-2'-O-TBDMS-3'-O-DMT-adenosine (27a): To the solution of 14 g (15.7 mmol) of the compound 26a in 189 mL of pyridine and 21 mL of methanol mixture were added 15.7 mL of 2 M aqueous solution of sodium hydroxide (31.4 mmol) dropwise with stirring at 0-5° C. during the course of 25 min. The reaction mixture was neutralized with 12 mL of 2 M HCl. The solvent was removed under diminished pressure and residue was extracted with two portions of 25 mL of chloroform. Organic layer was combined, washed with 50 mL of brine and dried over anhydrous $Na_2SO_4$. Flash chromatography with 6.5:2:1.5 chloroform/hexanes/acetone provided 11.0 g (88.9%) of the compound 27a. Yield is %. $^1$H NMR ($CDCl_3/H_2O$) δ −0.75 (s, 3H), −0.01 (s, 3H), 0.86 (s, 9H), 3.03 (t, 1H, $J_{5a,5b}$=12.8 Hz), 3.29 (s, 1H), 3.47 (br.d, 1H, $J_{5a,5b}$=12.8 Hz), 3.80 (s, 6H), 4.35 (d, 1H, J=4.9 Hz), 5.17 (dd, 1H, J=8 Hz, J=5 Hz), 5.93 (dd, 1H, J=12 Hz, J=2 Hz), 6.15 (d, 1H, J=8 Hz), 6.85 (dd, 4H, J=7 Hz, J=3 Hz), 7.23 (t, 1H, J=7.5 Hz), 7.30 (t, 2H, J=7 Hz), 7.48 (m, 4H), 7.52 (t, 2H, J=7.3 Hz), 7.62 (d, 3H, J=7.5 Hz), 8.03 (d, 2H, J=7.5 Hz), 8.14 (s, 1H), 8.77 (s, 1H), 9.07 (s, 1H). ESMS [$C_{44}H_{49}N_5O_7Si$ (M+Na)⁺ requires 787.3].

N⁴-Benzoyl-2'-O-TBDMS-3'-O-DMT-adenosine-5'-cyanoethyl-N,N-diisopropyl-phosphoramidite (16a): To the solution of 11.0 g (12.0 mmol) of the compound 27a, 9.2 mL (60.0 mmol) of collidine, 1.1 mL of N-methylimidazole in 88 mL of distilled THF were added 6.23 mL (24.0 mmol) of 2-cyanoethyl-N,N, diisopropyl-phosphonamidic chloride dropwise with stirring under Ar at room temperature. After 1.25 hrs the reaction mixture was diluted with 50 mL of ethylacetate and washed with 100 mL of saturated sodium bicarbonate and 100 mL of brine. The organic layer was separated and dried over 10 g of anhydrous $Na_2SO_4$. Flash chromatography with 5:4:1 ethylacetate/hexanes/triethylamine provided 9.0 g 77.7%) of the compound 16a. $^{31}$P NMR ($CDCl_3$) δ 143.97 and 144.14. ESMS 987.2 [$C_{53}H_{66}N_7O_8PSi$ (M+Na)⁺ requires 987.45 ].

Comparative $^1$H NMR data of structures 3'-O-DMT-2'-O-TBDMS nucleosides 27a, 27c, 27d, 27k, 16a, 16c, 16d, 16k and 5'-O-DMT-2'-O-TBDMS nucleosides 28-31.

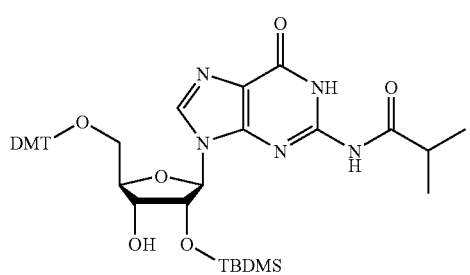

Structure (28)

TABLE 1

Comparative $^1$H NMR data of structures 27d, 16d and structure 28.

| Structure | H-1' | H-2' | H-3' | H-4' | H-5'ab | H-8 | CH | CH₃ |
|---|---|---|---|---|---|---|---|---|
| 27d | 5.97, d. J = 8.0 | 4.83, dd J = 8.12 | 4.24, d. J = 5 | 3.28, br.s. | 3.37, dd. J = 15.0, 2.5 2.98, d. J = 15.0 | 7.76, s. | 2.66, qq. J = 7 | 1.31, d., J = 7 1.27, d., J = 7 |
| 28 | 5.78, d. J = 7 and 5.72, d. J = 6.7 | 5.13, dd. J = 7, 5 and 4.87, dd. J = 7, 5.5 | 4.8, br.s. | 4.356-4.353, m. and 4.242-4.223, m. | 3.89, dd. J = 10, 2.5 3.54, dd. J = 10, 2.5 3.11 J = 10, 2.5 | 7.84, s. | 2.78, qq. J = 7 | 1.192, d. J = 7 1.179, d. J = 7 |
| 16d | 6.22, d., J = 7, 5 and 5.96, d., J = 5 | | | | | 8.21, s. and 8.08, s. | | |

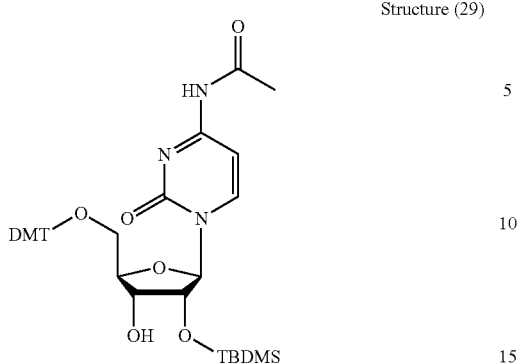

Structure (29)

TABLE 2

Comparative ¹H NMR data of structures 27c, 16c and structure 29.

| Structure | H-1' | H-2' | H-3' | H-4' | H-5'ab | H-5 | H-6 | —COCH₃ |
|---|---|---|---|---|---|---|---|---|
| 27c | 5.61, d. J = 4.1 | 4.78, br.s. | 4.43, br.s. | 4.08, t, J = 4.6 | 3.55, br.d. J = 12.5 3.16, br.d. J = 11.5 | 6.81, d. J = 7 | 7.21, d. J = 7 | 2.24, s. |
| 29 | 5.90, s. and 5.62, J = 5 | 4.34-436, m. | 4.20-428, m. | 4.10, br.d. J = 5 | 3.58, d.d. J = 11.5, 2 3.52, dd. J = 11.5, 2 | 7.12, d. J = 7 | 7.16, d. J = 7 | 2.25, s. |
| 16c | 5.83, d., J = 2 6.32, d., J = 5 | | | | | | | |

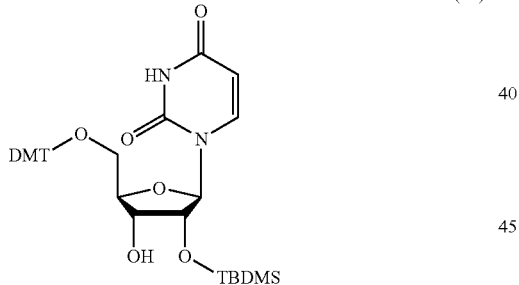

Structure (30)

TABLE 3

Comparative ¹H NMR data of structures 27k, 16k and structure 30.

| Structure | H-1' | H-2' | H-3' | H-4' | H-5'ab | H-5 | H-6 |
|---|---|---|---|---|---|---|---|
| 27k | 5.66, d. J = 4.9 | 4.28, t. J = 4.7 | 4.07, t, J = 4.3 | 3.64-3.65, br.m. | 3.53, br.dd. J = 13.7, 4.4 3.19, br.dd. J = 13.7, 7.6 | 5.68, d. J = 8.1 | 7.68, d. J = 8.1 |
| 30 | 5.95, d. J = 2.8 and 5.69, d. J = 4.6 | 4.49, t. J = 5 and 4.19, t. J = 5 | 4.05-4.08, m. | 4.10-4.11, br.s. | 3.49-3.51, m. 3.90-3.93, m. | 5.30, d. J = 8.2 5.73, d. J = 8.1 | 7.95, d. J = 8.2 7.75, d, J = 7.2 |
| 16k | 6.00, d., J = 4.5 and 6.38, d., | | | | 7.75, d. J = 8.2 7.92, | | |

TABLE 3-continued

Comparative $^1$H NMR data of structures 27k, 16k and structure 30.

| Structure | H-1' | H-2' | H-3' | H-4' | H-5'ab | H-5 | H-6 |
|---|---|---|---|---|---|---|---|
| | J = 7.1 | | | | | | d. J = 8.2 |

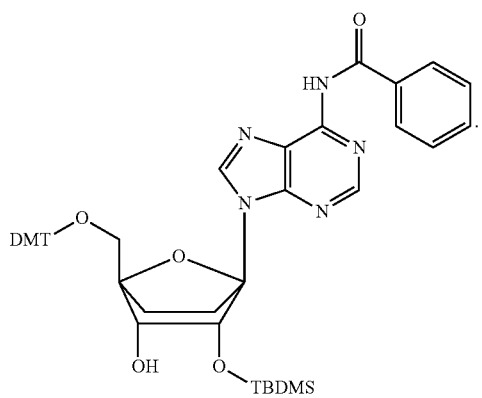

Structure (31)

TABLE 4

Comparative $^1$H NMR data of structures 27a, 16a and structure 31.

| Structure | H-1' | H-2' | H-3' | H-4' | H-5'ab | H-2 | H-8 |
|---|---|---|---|---|---|---|---|
| 27a | 6.15, d. J = 8 | 5.17, dd. J = 8, 4.8 | 4.35, d. J = 4.8 | 3.29, br.s. | 3.47, br.dd. J = 11.5, 2 3.04, t. J = 12.3 | 8.14, s. | 8.76, s. |
| 31 | 5.82, d. J = 7 | 5.00, t. J = 5.5 | 437-435, m. | 4.27, dd. J = 7, 3.4 | 3.54, dd. J = 10.7, 3 3.40, dd. J = 10.7, 3.8 | 8.21, s. | 8.71, s. |
| 16a | 6.53, d., J = 7 and 6,24, d., J = 4.5 | | | | | 8.54, s. and 8.48, s. | 8.87, s. and 8.79, s. |

EXAMPLE 5

Synthesis of 2'-O-TBDMS-3'-O-DMT-uridine-5'-succinyl-CPG

2'-O-TBDMS-3'-O-DMT-Uridine-5'-succinate: To the solution of 2.0 g (3.03 mmol) of the compound 27k and 0.11 g (0.91 mmol) of DMAP in 20 mL of pyridine were added 0.9 g (9.1 mmol) of succinic anhydride with stirring at 37° C. After 12 hrs the reaction mixture was diluted with 30 mL of chloroform and washed with 50 mL of brine. The organic layer was separated and dried over anhydrous $Na_2SO_4$. Flash chromatography with 5:3:2:0.01:0.05 chloroform/hexanes/acetone/pyridine/methanol provided 1.8 g (75.9%) of 2'-O-TBDMS-3'-O-DMT-uridine-5'-succinate. $^1$H NMR (CDCl$_3$/D$_2$O) δ 0.05 (s, 3H), 0.07 (s, 3H), 0.96 (s, 9H), 2.21 (dt, 1H, J=17 Hz, J=6 Hz), 2.40-2.46 (m, 1H), 2.51 (dt, 1H, J=17 Hz, J=6 Hz), 2.60-2.66 (m, 1H), 3.42 (t, 1H, J=3.3 Hz), 3.77 (s, 6H), 3.95-3.98 (m, 2H), 4.11 (br.d, 1H, J=12.8 Hz), 4.16 (m, 1H), 5.72 (d, 1H, J=2.8 Hz), 5.74 (d, 1H, J=8.1 Hz), 6.79 (dd, 4H, J=9 Hz, J=1.9 Hz), 7.21 (t, 1H, J=7 Hz), 7.25 (t, 2H, J=7 Hz), 7.38 (d, 4H, J=8.9 Hz), 7.48 (d, 2H, J=7.2 Hz), 7.61 (d, 1H, J=8.2 Hz), 7.72 (t, 1H, J=5.9 Hz), 8.61 (br.d, 1H, J=4.4 Hz). ESMS 784.2 [$C_{40}H_{48}N_2O_{11}$Si (M+Na)$^+$ requires 783.9].

2'-O-TBDMS-3'-O-DMT-uridine-5'-succinyl-CPG: To the suspension of 18 g of amino-lcca-CPG and 3.6 mL of triethylamine in 60 mL of DMF was added the solution of 1.8 g (2.3 mmol) of O-TBDMS-3'-O-DMT-uridine-5'-succinate, 0.408 g (3.55 mmol) N-hydroxysuccinimide and 0.586 g (2.76 mmol) of DCC in 4 mL of DMF. The reaction mixture was warmed to 37° C. After 16 hrs CPG was filtered, washed with 3×20 mL portions of acetonitrile, capped with acetic anhydride in pyridine/N-methylimidazole mixture and washed 3×20 mL portions of acetonitrile. The solid support was dried under diminished pressure and nucleoside loading was measured by DMT removal procedure yielding 18 g of final product with 44.2 μmol/g loading.

Example 6

Oligonucleotide Synthesis: The following oligonucleotides (Table 5) were synthesized using 3'→5' directed standard RNA phosphoramidite chemistry in 1 μmole scale. The syntheses were performed on Expedite 8900 synthesizer using standard RNA 1 μmole cycle.

Following synthesis, the controlled pore glass (CPG) solid support was transferred to a 2 ml microfuge tube. Oligonucleotides were cleaved from the CPG and deprotected by incubation for 30 min at 65° C. in 1 ml of 40% methylamine solution in water. The supernatant was removed and the CPG was washed with 1 ml of water; supernatants were pooled and dried. The t-butyl-dimethylsilyl protecting group was removed from the RNA residue by treatment with 250 ul of fresh anhydrous triethylammonium-trihydrogen fluoride at room temperature in ultrasonic bath for 2 hours. The oligonucleotide was precipitated by 1.5 ml of n-butanol; the sample was cooled at −70° C. for 1 hour then centrifuged at 10,000 g for 10 minutes. The supernatant was decanted, the pellet was washed with n-butanol one more time.

The oligonucleotides were then purified by reverse-phase HPLC using a linear gradient of acetonitrile in 0.1 M triethylammonium acetate (TEAA) pH 7.2. The entire sample was loaded on a Hamilton PRP-1 column (1.0 cm×25 cm) and eluted with a linear 5% to 50% acetonitrile gradient over 40 minutes. Samples were monitored at 260 nm and peaks corresponding to the desired oligonucleotide species were collected, pooled, and lyophilized. The oligonucleotide samples were dissolved in 200 ul of sterile water and precipitated by adding 1 ml of 2% LiClO$_4$, followed by centrifuging at 10,000 g for 10 minutes. The supernatant was decanted, the pellet was washed with 10% aqueous acetone.

The standard dT and cholesterol corresponding solid supports suitable for oligonucleotide synthesis have been used.

TABLE 5

Oligonucleotide sequences synthesized by conventional method.

| | |
|---|---|
| SEQ ID No. 1 | rCrArGrGrUrGrCrArGrArGrCrCrUrUrGr CrCrCTT |
| SEQ ID No. 2 | rCrArGrGrUrGrCrArGrArGrCrCrUrUrGr CrCrCTT-Cholesterol |

The following oligonucleotides (Table6) were synthesized using 5'→3' directed reverse phosphoramidite chemistry in 1 mmole scale. The same synthesis cycle and ancillary reagents as in standard process have been used for reverse synthesis. The reverse rC-lcaa-CPG was used in all oligonucleotide syntheses. The 3'-modifications of the oligonucleotides SEQ ID No. 2-4 have been introduced by using cholesterol, PEG-2000 or HEG phosphoramidites respectively.

TABLE 6

Oligonucleotide sequences synthesized by reverse method.

| | |
|---|---|
| SEQ ID No. 1 | rCrArGrGrUrGrCrArGrArGrCrCrUrUrGr CrCrCTT |
| SEQ ID No. 2 | rCrArGrGrUrGrCrArGrArGrCrCrUrUrGr CrCrCTT-Cholesterol |
| SEQ ID No. 3 | rCrArGrGrUrGrCrArGrArGrCrCrUrUrGr CrCrCTT-PEG/2000 |
| SEQ ID No. 4 | rCrArGrGrUrGrCrArGrArGrCrCrUrUrGr CrCrCTT-HEG |

Crude oligonucleotides were analyzed by CE and ESI mass-spectrometry.

A vast number of applications are possible for easy attachment at 3'-End of an oligonucleotide. Some of the examples are outlined in FIG. 7:

1. For attachment of bulky molecules at the 3'-end of the RNA, such as cholesterol, long chain aliphatic chains such as C-18, triethylene glycols, hexaethylene glycols. Direct coupling with these amidites can be achieved easily.
2. Attachment of Polyethylene Glycols such as PEG 2000 amidie and PEG 4000 amidites at the 3'-end of the RNA molecule.
3. For Easy attachment of 3'-thiol modification. 3'-Disulfides from readily available amidites, viz., C-3 disulfide, C-6 disulfide.
4. 3'-Biotin attachment via biotin amidite in a single step and avoiding biotin CPG for this purpose.
5. Modification of 3'-End of the Sense Strand of siRNA. The modification of the overhang of the sense strand (3'-End) of siRNA is not expected to affect targeted mRNA recognition, as the antisense siRNA strand guides target recognition. Useful modification for improvement of delivery of siRNA can be easily designed.

TABLE 3

Comparative $^1$H NMR data of structures 27k, 28k and formula 8.

| Structure | H-1' | H-2' | H-3' | H-4' | H-5'ab | H-5 | H-6 |
|---|---|---|---|---|---|---|---|
| 27k | 5.66, d. $J = 4.9$ | 4.28, t. $J = 4.7$ | 4.07, t, $J = 4.3$ | 3.64-3.65, br.m. | 3.53, br.dd. $J = 13.7, 4.4$ 3.19, br.dd. $J = 13.7, 7.6$ | 5.68, d. $J = 8.1$ | 7.68, d. $J = 8.1$ |
| Formula 8 | 5.95, d. $J = 2.8$ and 5.69, d. $J = 4.6$ | 4.49, t. $J = 5$ and 4.19, t. $J = 5$ | 4.05-4.08, m. | 4.10-4.11, br.s. | 3.49-3.51, m. 3.90-3.93, m. | 5.30, d. $J = 8.2$ 5.73, d. $J = 8.1$ | 7.95, d. $J = 8.2$ 7.75, d, $J = 7.2$ |
| 28k | 6.00, d., $J = 4.5$ and 6.38, d., $J = 7.1$ | | | | | 7.75, d. $J = 8.2$ 7.92, d. $J = 8.2$ | |

We summarize in the notes below the various innovations, advantages and possibilities, and some product and process details of the present invention. This list is meant to serve as a convenient and illustrative summary, and is not complete, exhaustive or limiting.

1. Derivatized nucleoside and phosphoramidites of general formula 1.

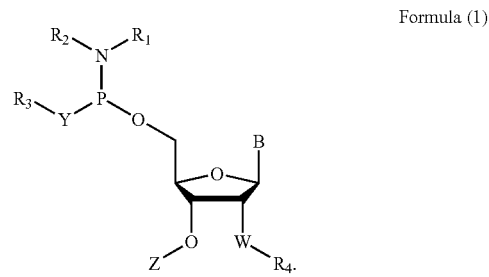

Formula (1)

wherein

Y is oxygen or sulfur;

W is oxygen, nitrogen, sulfur or fluorine;

$R_4$ is silyl ether such as TBDMS, triisopropylsilyl oxymethylene, Fmoc, alkyl, aryl, or acetyl, when W is not sulphur; but in case when W is sulfur $R_4$ is benzoyl, acetyl or disulfide;

Z is DMT, MMT, TMT protecting group;

$R_1$ and $R_2$ are independently selected from an alkyl or aryl group;

$R_3$ is cyanoethyl, alkyl or aryl.

2. Derivatized nucleoside attached to solid support of general formula 2.

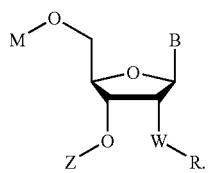

Formula (2)

wherein

M is a hydrogen radical and may comprise formula Y—CO—;

Y is a chain of atoms from 2 to 20 in length, consisting essentially of a hydrocarbon chain optionally substituted by one or more heteroatoms independently selected from the group consisting of oxygen, nitrogen and sulfur; connected to CPG, polystyrene or any other solid support suitable for oligonucleotide synthesis;

W is oxygen, nitrogen, sulfur or fluorine;

R is silyl ether such as TBDMS, triisopropylsilyl oxymethylene, Fmoc, alkyl, aryl, amino or acetyl, when W is not sulphur; but in the case when W is sulfur R is benzoyl, acetyl or disulfide;

Z is DMT, MMT, TMT protecting group;

3. A method for reverse, via 5' to 3' direction of oligonucleotide bond formations shown in formula 10 in synthetic RNA oligomers. The RNA could consist of natural or modified nucleo bases, gapmers, phosphodiesters, phosphorothiates, phosphoselenates. The synthesis may be performed on automated, semi automated DNA/RNA or other synthesizers or manually. The synthesis can be performed at various scales from microgram to kilogram scales.

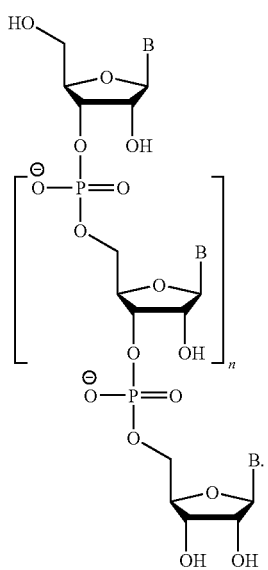

Formula (10)

4. A method of attachment of modifications to 3'-terminus of RNA molecules using corresponding phosphoramidites (Formula 11), wherein L is a modification such as biotin or cholesterol, or selected from the group consisting of fluorophore, quencher dyes, polyethylene glycols, and peptides.

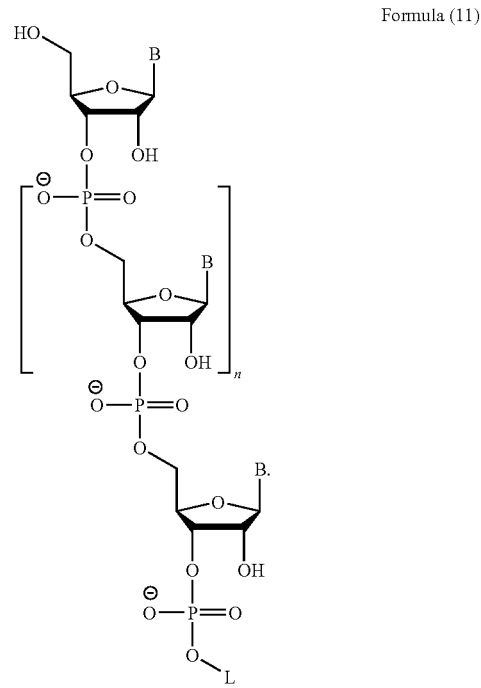

Formula (11)

5. Synthesis of automated high purity RNA using Reverse Direction (5'→3') RNA synthesis resulting in high purity RNA.

6. 3'-Conjugation of RNA with macromolecules such as Cholesterol, hexaethyloxyglycols (HEG) and Polyethylene glycols (PEG).

7. Application of the automated RNA synthesis in the reverse Direction (5'→3'), resulting in the absence of M+1 oligonucleotide impurities.

8. The modified nucleosides incorporated by this method mentioned above could consists of one or more of purine or pyrimidine modifications, such as but not limited to, 5-Fluoro-U, 5-Fluoro dU, 5-fluoro-dC, 5-Fluro-rC, pseudouridine, 5-methyl-dU, 5-methyl-rU, 5-methyl-dC, 5-methyl-rC, 5-bromo-dU, 5-bromo-rU, 5-bromo-dC, 5-bromo-rC, 5-iodo-dU, 5-iodo-rU, 5-vinyl-dU, 5-vinyl-rU, 5-vinyl thymidine, N-3 methyldeoxy uridine, N-3 methyl-ribouridine, N-3 methyl thymidine, 4-thio uridine, 4-thio-2'-deoxyuridine, 2,6-diaminopurine deoxy riboside, N-3 methyl ribothymidine, 2,6-diaminopurine riboside, 8-bromo 2'-deoxy adenosine, 8-bromo-r-adenosine, 8-oxo-deoxy adenosine, 8-oxo-riboadenosine, 8-oxo-2'-deoxy-adenosine, 8-oxo-riboadenosine, 8-oxo-deoxy inosine, 8-oxo-ribo inosine, 8-bromo-deoxy inosine, 8-bromo-ribo-inosine, N-1 methyl-riboadenosine, N-1 methyl-2'-deoxy adenosine, N-1 methyl 2'-deoxy inosine, N-1 methyl riboadenosine, N-1 methyldeoxy guanosine, N-1-methyl-riboguanosine, etheno adenosine, etheno 2'-deoxy adenosine, purine 2'-deoxy riboside, purine-ribonucleoside, 2-aminopurine-2'-deoxyriboside, 2-aminopurine-ribonucleoside.

9. Labelling of internal positions of an RNA synthesized by this method is achievable with chromophores such as, but not limited to Fluoroscein-C-5 dT, Dabcyl-C-5 thymidine, internal carboxyl group 5-dU-methylacrylate, biotin dT (biotin wattached via spacer to C-5 of dU), amino-dT (terminal amino attached via C-6 spacer to C-5 dU).

10. The sugar modification of modified nucleosides could consist of 2'-deoxy-2'-fluoro ribo nucleosides (2'-F-ANAs) such as A, C, G, U, Inosine and modified nucleosides containing 2'-Fluoro, in one or more positions of an RNA or DNA sequence synthesized by the method of this invention.

11. The sugar modification of modified nucleosides could consist of 2'-deoxy-2'-methoxy ribo nucleosides (2'-OMe-) such as A, C, G, U, Inosine and modified nucleosides containing 2'-methoxy, in one or more positions of an RNA or DNA sequence synthesized by this method.

12. The sugar modification of modified nucleosides could consist of 2'-deoxy-2'-amino ribo nucleosides (2'-NH2) such as A, C, G, U, Inosine and modified nucleosides containing 2'-amino, in one or more positions of an RNA or DNA sequence synthesized by this method.

13. The sugar modification of modified nucleosides could consist of 2'-deoxy-2'-terminal amino ribo nucleosides (2'-terminal NH2), attached via spacer from 2-10 atoms on nucleosides such as A, C, G, U, Inosine and modified nucleosides containing 2'-terminal amino, in one or more positions of an RNA or DNA sequence synthesized by this method.

14. The sugar modification of modified nucleosides could consist of 2'-deoxy-2'-methoxy ethoxy ribo nucleosides (2'-MOE), such as A, C, G, U, Inosine and modified nucleosides containing 2'-MOE, in one or more positions of an RNA or DNA sequence synthesized by this method.

15. The sugar modification of modified nucleosides could consist of other 2'-O-alkyl groups, such as 2'-deoxy-2'-ethoxy, propargyl, butyne ribo nucleosides (2'-OEt, O-Propargyl, 2'-O-Butyne), such as A, C, G, U, Inosine and modified nucleosides containing 2'-2'-OEt, O-Propargyl, 2'-O-Butyne, in one or more positions of an RNA or DNA sequence synthesized by this method.

16. The sugar modification of modified nucleosides could consist of 2'-deoxy-2'-fluoro arabino nucleosides (2'-F-ANAs) such as A, C, G, U, Inosine and modified nucleosides containing 2'-F-ANAs), in one or more positions of an RNA or DNA sequence synthesized by this method.

17. The sugar modification of modified nucleosides could consist of 2'-deoxy-2'-fluoro 4'-thioarabino nucleosides (4'-S-FANAs) such as A, C, G, U, Inosine and modified nucleosides containing 4'-S-FANAs in one or more positions of an RNA or DNA sequence synthesized by this method.

18. The RNA may be carried out with one or more 2'-5'-linkage within the sequence, at the 3'-end of the sequence or at the 5'-end of the sequence.

19. The RNA having a 3'-end, may be synthesized by the method of this invention containing reverse attached deoxy nucleosides such as dT, dC, dG, thymidine, attached via their 3'-hydroxyl function.

20. The RNA having a 3'-end may be synthesized by the method of this invention containing reverse attached ribonucleosides such as rA, rC, rG, rU, attached via their 2' or 3'-hydroxyl function.

21. The reverse RNA synthesis may be achieved comprising 2'-triisopropylsilyloxy methyl (TOM) protecting group.

22. The reverse RNA synthesis may be achieved comprising 2'-t-butyldithiomethyl (DTM) protecting group.

23. The reverse RNA synthesis may be achieved comprising the modified base comprising 2'-deoxy-2'-fluoro-beta-D_arabinonucleic acid (FANA).

24. The reverse RNA synthesis may be achieved comprising the modified base comprising 4'-thio-2'-deoxy-2'-fluoro-beta-D_arabinonucleic acid (4'-Thio-FANA).

25. The reverse RNA synthesis may be achieved comprising the modified sugar using 2'-OMethyl modification.

26. The reverse RNA synthesis may be achieved by using Bicyclic locked nucleic acids (LNA's).

27. The reverse RNA synthesis may use the modified sugar comprising altritol sugar modified oligonucleotides (ANA).

28. The reverse RNA synthesis may comprise the step of conjugation of lipophilic or hydrophobic groups at the 3'-end of the RNA either through a amidite function on the hydrophobic moiety or through an amino linker at the 3'-end of reverese synthesized oligonucleotide having a terminal amino group. The later synthesis involving a coupling step between amino at the 3'-terminal oligonucleotide and carboxylic function on the lipophilic moiety. The lipophilic moieties consist of various glycol, such as triethylene glycol, hexaethylene glycol, polyethylene glycols, various lipids.

29. The reverse RNA synthesis may comprise the step of conjugation of peptides, such as cell penetrating peptides (CPPs) or membrane permeant peptide (MPPs) utilizing either the free amine function of such peptides and a 3'-terminal carboxylic function on the reverse synthesized RNA. The CPPs and MPPs having an appropriate carboxyl function can be coupled to the free terminal amino function of a 3'-end of the reverse synthesized RNA.

30. The reverse RNA synthesis comprise the 2'-5'-linked DNA units or 2'-5'-RNA units within the sequence, at the 3'-end of the sequence or at the 5'-end of the sequence.

Having described the invention as above,

We claim:

1. A phosphoramidite having formula (1),

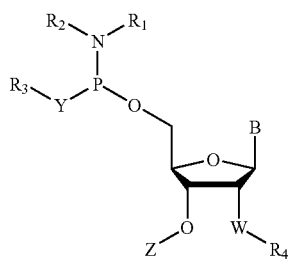

Formula (1)

where,

Y is an oxygen atom or a sulfur atom;

W is selected from the group consisting of an oxygen diradical, a N—H diradical and a fluorine radical, and $R_4$ is selected so that, if W is an oxygen diradical, then $R_4$ is tert butyl dimethyl silyl (TBDMS) or triisopropylsilyloxymethylene (TOM);

if W is a N—H diradical, then $R_4$ is of the form $R_5{}^x$ where x is selected from the group consisting of fluorenylmethyloxycarbonyl (Fmoc), trifluoroacetyl, acetyl, alkanoyl, and aroyl; and if W is a fluorine radical, then $R_4$ is not present;

B is selected from the group of nucleoside base radicals consisting of -9-($N^6$-benzoyladeninyl)-, 9-($N^6$-acetyladeninyl)-, 9-($N^6$-tert butyl phenoxyacetyladeninyl)-, 9-($N^6$-phenoxyacetyladeninyl)-, 9-($N^6$-isopropyl phenoxyacetyladeninyl)-, 1-($N^4$-benzoylcytosinyl)-, 1-($N^4$-acetylcytosinyl)-, 1-($N^4$—(N,N-dimethylformamidinyl)cytosinyl)-, 1-($N^4$-phenoxyacetylcytosinyl)-, 1-($N^4$-tertbutylphenoxyacetylcytosinyl)-, 1-($N^4$-isopropyl phenoxyacetylcytosinyl)-, 9-($N^2$-isobutyrylguaninyl)-, 9-($N^2$-tertbutylphenoxyacetylguaninyl)-, 9-($N^2$-isopropylphenoxyacetylguaninyl)-$N^4$-phenoxyacetylcytosinyl)-, 1-($N^4$-tertbutylphenoxyacetylcytosinyl)-, 1-($N^4$-isopropyl phenoxyacetylcytosinyl)-, and 1-uracilyl-;

or, B is a modified nucleoside base radical selected from the group consisting of 1-($N^4$-benzoyl-5-methylcytosinyl)-, 1-($N^4$—(N,N-dimethylformamidinyl)-5-methylcytosinyl)-, 1-($N^4$-acetyl-5-methylcytosinyl)-, 1-(5-methyl-uracilyl)-, -(5-fluoro-uracilyl)-, 1-($N^4$-benzoyl-5-fluorocytosinyl)-, 9-($N^6$-benzoyl-7-deazaadeninyl)-, 9-($N^6$—(N,N-dimethylformamidinyl)-7-deazaadeninyl)-, 9-($N^2$-isobutyryl-7-deazaguaninyl)-, and 9-($N^2$—(N,N dimethylformamidinyl)-7-deazaguaninyl)-;

Z is a protecting group selected from the group consisting of dimethoxytriphenylmethyl (DMT), monomethoxytriphenylmethyl (MMT) and trimethoxytriphenylmethyl (TMT);

$R_1$ is an alkyl or aryl radical;

$R_2$ is an alkyl or aryl radical; and, $R_3$ is a cyanoethyl radical, alkyl radical or aryl radical.

2. A derivatized nucleoside having a structure of formula 2,

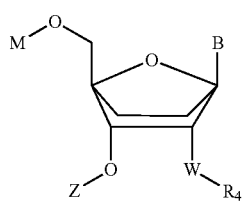

Formula (2)

where,

M is a hydrogen radical or a linker;

if M is a linker, then it is represented by the formula Y—C(O) and, optionally, connected to a solid support suitable for oligonucleotide synthesis, wherein Y is a chain of between 2 and 20 carbons, selected from the group consisting of alkyl, alkenyl, cycloalkyl, aryl, and aralkyl, in a hydrocarbyldiradical moiety, optionally comprising intervening —O—, —S—, —S(O)$_2$—, —C(O)—, and —NR$_6$—, where R$_6$ is a hydrogen radical, or a substituted $C_1$ to $C_{20}$ alkyl or a substituted aralkyl;

W is selected from the group consisting of an oxygen diradical, a N—H diradical and a fluorine radical, and $R_4$ is selected so that, if W is an oxygen diradical, then $R_4$ is tert butyl dimethyl silyl (TBDMS) or triisopropylsilyloxymethylene (TOM);

if W is a N—H diradical, then $R_4$ is of the form $R_5^x$ where x is selected from the group consisting of fluorenylmethyloxycarbonyl (Fmoc), trifluoroacetyl, acetyl, alkanoyl, and aroyl; and if W is a fluorine radical, then $R_4$ is not present;

B is selected from the group of nucleoside base radicals consisting of -9-($N^6$-benzoyladeninyl)-, 9-($N^6$-acetyladeninyl)-, 9-($N^6$-tert butyl phenoxyacetyladeninyl)-, 9-($N^6$-phenoxyacetyladeninyl)-, 9-($N^6$-isopropyl phenoxyacetyladeninyl)-, 1-($N^4$-benzoylcytosinyl)-, 1-($N^4$-acetylcytosinyl)-, 1-($N^4$—(N,N-dimethylformamidinyl)cytosinyl)-, 1-($N^4$-phenoxyacetylcytosinyl)-, 1-($N^4$-tertbutylphenoxyacetylcytosinyl)-, 1-($N^4$-isopropyl phenoxyacetylcytosinyl)-, 9-($N^2$-isobutyrylguaninyl)-, 9-($N^2$tertbutylphenoxyacetylguaninyl)-, 9-($N^2$-isopropylphenoxyacetylguaninyl)-, $N^4$-phenoxyacetylcytosinyl)-, 1-($N^4$-tertbutylphenoxyacetylcytosinyl)-, 1-($N^4$-isopropyl phenoxyacetylcytosinyl)-, and 1-uracilyl-;

or B is selected from the group of modified nucleoside base radicals selected from the group consisting of 1-($N^4$benzoyl-5-methylcytosinyl)-, 1-($N^4$—(N,N-dimethylformamidinyl)-5-methylcytosinyl)-, 1-($N^4$acetyl-5-methylcytosinyl)-, 1-(5-methyl-uracilyl)-, -(5-fluoro-uracilyl)-, 1-($N^4$-benzoyl-5-fluorocytosinyl)-, 9-($N^6$-benzoyl-7-deazaadeninyl)-, 9-($N^6$—(N,N-dimethylformamidinyl)-7-deazaadeninyl)-, 9-($N^2$-isobutyryl-7-deazaguaninyl)-, and 9-($N^2$—(N,N-dimethylformamidinyl)-7-deazaguaninyl)-; and, Z is a protecting group selected from the group consisting of dimethoxytriphenylmethyl (DMT), monomethoxytriphenylmethyl (MMT) and trimethoxytriphenylmethyl (TMT).

3. A process of synthesizing RNA oligomers represented by Formula (3) wherein oligonucleotide is synthesized in the 5'-to 3'-direction,

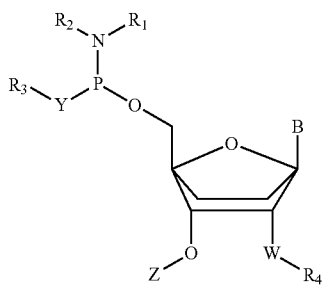

Formula (2)

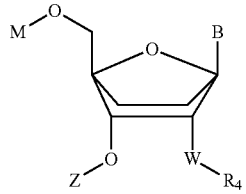

Formula (3)

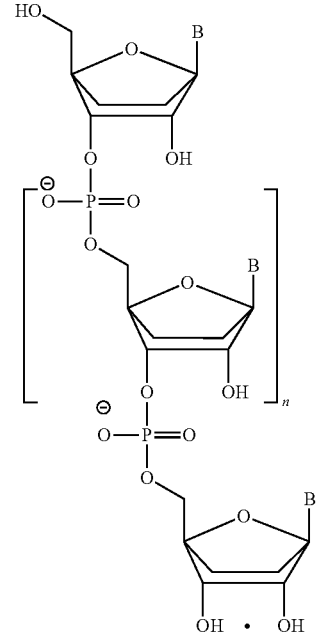

and wherein the variables in formulas 1, 2 and 3 are defined as follows:

Y is an oxygen atom or a sulfur atom;

W is selected from the group consisting of an oxygen diradical, a N—H diradical and a fluorine radical, and $R_4$ is selected so that, if W is an oxygen diradical, then $R_4$ is tert butyl dimethyl silyl (TBDMS) or triisopropylsilyloxymethylene (TOM);

if W is a N-H diradical, then $R_4$ is of the form $R_s^x$ where x is selected from the group consisting of fluorenylmethyloxycarbonyl (Fmoc), trifluoroacetyl, acetyl, alkanoyl, and aroyl;

if W is a fluorine radical, then $R_4$ is not present;

B is selected from the group of nucleoside base radicals consisting of -9-($N^6$-benzoyladeninyl)-, 9-($N^6$-acetyladeninyl)-, 9-($N^6$-tert butyl phenoxyacetyladeninyl)-, 9-($N^6$-phenoxyacetyladeninyl)-, 9-($N^6$-isopropyl phenoxyacetyladeninyl)-, 1-($N^4$-benzoylcytosinyl)-, 1-($N^4$-acetylcytosinyl)-, 1-($N^4$—(N,N- dimethylformamidinyl)cytosinyl)-, 1-($N^4$phenoxyacetylcytosinyl)-, 1-($N^4$-tertbutylphenoxyacetylcytosinyl)-, 1-($N^4$-isopropyl phenoxyacetylcytosinyl)-, 9-($N^2$-isobutyrylguaninyl)-, 9-($N^2$-tertbutylphenoxyacetylguaninyl)-, 9-($N^2$-isopropylphenoxyacetylguaninyl)-$N^4$-phenoxyacetylcytosinyl)-, 1-($N^4$-tertbutylphenoxyacetylcytosinyl)-, 1-($N^4$-isopropyl phenoxyacetylcytosinyl)-, and 1-uracilyl-;

or, B is a modified nucleoside base radical selected from the group consisting of 1-($N^4$-benzoyl-5-methylcytosinyl)-, 1-($N^4$—(N,N-dimethylformamidinyl)-5-methylcytosinyl)-, 1-($N^4$-acetyl-5-methylcytosinyl)-, 1-(5-methyl-uracilyl)-, -(5-fluoro-uracilyl)-, 1-($N^4$-benzoyl-5-fluorocytosinyl)-, 9-($N^6$-benzoyl-7-deazaadeninyl)-, 9-($N^6$—(N,N-dimethylformamidinyl)-7-deazaadeninyl)-,9-($N^2$-isobutyryl-7-deazaguaninyl)-, and 9-($N^2$—(N,N-dimethylformamidinyl)-7-deazaguaninyl)-;

Z is a protecting group selected from the group consisting of dimethoxytriphenylmethyl (DMT), monomethoxytriphenylmethyl (MMT) and trimethoxytriphenylmethyl (TMT);

$R_1$ is an alkyl or aryl radical;

$R_2$ is an alkyl or aryl radical;

$R_3$ is a cyanoethyl radical, alkyl radical or aryl radical;

M is a hydrogen radical or a linker;

if M is a linker, then it is represented by the formula Y—C(O) and optionally connected to a solid support suitable for oligonucleotide synthesis, wherein Y is a chain of between 2 and 20 carbons, selected from the group consisting of alkyl, alkenyl, cycloalkyl, aryl, and aralkyl, in a hydrocarbyldiradical moiety, optionally comprising intervening —O—, —S—, —S(O)$_2$—, —C(O)—, and —NR$_6$, where R$_6$ is a hydrogen radical, or a substituted $C_1$ to $C_{20}$ alkyl or a substituted aralkyl;

n is an integer between 0 and 100; and wherein, the process of RNA synthesis in the 5'->3' direction comprises the steps of:

(a) providing a support attached nucleoside represented by formula (2);

(b) placing one or more appropriate phosphoramidites represented by formula (1) in an oligonucleotide synthesizer;

(c) performing oligonucleotide synthesis and coupling on the synthesizer;

(d) detaching synthesized oligonucleotide from the solid support;

(e) removing the base protecting group or groups, if present, from the oligonucleotide;

(f) removing the sugar silyl protecting group or groups;

(g) precipitating crude oligonucleotide;

(h) optionally, analyzing the crude oligonucleotide for purity.

\* \* \* \* \*

(12) INTER PARTES REVIEW CERTIFICATE (3883rd)
United States Patent
Srivastava et al.

(10) Number: US 8,309,707 K1
(45) Certificate Issued: Feb. 18, 2025

(54) RNA SYNTHESIS-PHOSPHORAMIDITES FOR SYNTHETIC RNA IN THE REVERSE DIRECTION, AND APPLICATION IN CONVENIENT INTRODUCTION OF LIGANDS, CHROMOPHORES, AND MODIFICATIONS OF SYNTHETIC RNA AT THE 3'-END

(75) Inventors: Suresh C. Srivastava; Divya Pandey; Naveen P. Srivastava; Satya P. Bajpai

(73) Assignee: CHEMGENES CORPORATION

Trial Number:

IPR2023-00875 filed Apr. 24, 2023

Inter Partes Review Certificate for:

Patent No.: 8,309,707
Issued: Nov. 13, 2012
Appl. No.: 12/584,625
Filed: Sep. 8, 2009

The results of IPR2023-00875 are reflected in this inter partes review certificate under 35 U.S.C. 318(b).

INTER PARTES REVIEW CERTIFICATE
U.S. Patent 8,309,707 K1
Trial No. IPR2023-00875
Certificate Issued Feb. 18, 2025

AS A RESULT OF THE INTER PARTES REVIEW PROCEEDING, IT HAS BEEN DETERMINED THAT:

Claims 1 and 2 are cancelled.

\* \* \* \* \*